(12) United States Patent
Sato et al.

(10) Patent No.: US 7,250,522 B2
(45) Date of Patent: Jul. 31, 2007

(54) METHOD FOR SELECTIVE PREPARATION OF ARYL 5-THIO-β-D-ALDOHEXOPYRANOSIDES

(75) Inventors: Masakazu Sato, Tokyo (JP); Hiroyuki Kakinuma, Tokyo (JP); Hajime Asanuma, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 237 days.

(21) Appl. No.: 10/521,809

(22) PCT Filed: Aug. 8, 2003

(86) PCT No.: PCT/JP03/10159

§ 371 (c)(1),
(2), (4) Date: Jan. 21, 2005

(87) PCT Pub. No.: WO2004/014930

PCT Pub. Date: Feb. 19, 2004

(65) Prior Publication Data

US 2005/0256317 A1    Nov. 17, 2005

(30) Foreign Application Priority Data

Aug. 9, 2002  (JP) ............................ 2002-233015
Apr. 1, 2003  (JP) ............................ 2003-097839

(51) Int. Cl.
*C07D 335/02* (2006.01)
(52) U.S. Cl. ...................................... 549/28
(58) Field of Classification Search ................. 549/28
See application file for complete search history.

(56) References Cited

U.S. PATENT DOCUMENTS

| | | | |
|---|---|---|---|
| 6,555,519 B2 * | 4/2003 | Washburn ........................ | 514/3 |
| 6,602,899 B1 * | 8/2003 | Barberousse et al. ........ | 514/432 |
| 6,872,706 B2 * | 3/2005 | Fujikura et al. .............. | 514/25 |
| 2004/0063646 A1 | 4/2004 | Fujikura et al. | |

FOREIGN PATENT DOCUMENTS

| | | |
|---|---|---|
| EP | 850948 A1 | 7/1998 |
| EP | 1213296 A1 | 6/2002 |
| EP | 1270584 A1 | 1/2003 |
| EP | 1338603 A1 | 8/2003 |
| EP | 1 405 859 A1 | 4/2004 |
| JP | 10-237089 A | 9/1998 |
| WO | WO 01/16147 A1 | 3/2001 |
| WO | WO 01/68660 A1 | 9/2001 |
| WO | WO 01/74834 A1 | 10/2001 |
| WO | WO 01/74835 A1 | 10/2001 |
| WO | WO 02/36602 A1 | 5/2002 |
| WO | WO 02/053573 A1 | 7/2002 |
| WO | WO 03/000712 A1 | 1/2003 |

OTHER PUBLICATIONS

Bozo, et al. "Synthesis of 4-cyanophenyl and 4-nitrophenyl 1,5-dithio-L- and -D-arabinopyranosides possessing antithrombotic activity"., *Carbohydrate Research*, 1998, 311, pp. 191-202.

K.D. Randell, et al. Synthesis and glycosides inhibitory activity of 5-thioglucopyranosylamines. Molecular modeling of complexes with glucoamilase., *Carbohydrate Research*, 1999, 321, pp. 143-156.

H. Yuasa, et al. Relative Nucleophilicity of the Two Sulfur Atoms in 1,5-Dithioglucopyranoside., *Angew.Chem.Int.Ed.Engl.*, 1997, 36(8), pp. 868-870.

* cited by examiner

*Primary Examiner*—Deborah C. Lambkin
(74) *Attorney, Agent, or Firm*—Sughrue Mion, PLLC

(57) ABSTRACT

The present invention provides a method for preparing an aryl 5-thio-β-D-aldohexopyranoside derivative of Formula (III), which comprises reacting a 5-thio-D-aldohexopyranose derivative of Formula (I) with Ar-OH of Formula (II) in the presence of a phosphine represented by $PR^{11}R^{12}R^{13}$ and an azo reagent represented by $R^{21}$—N=N—$R^{22}$ in accordance with the following scheme

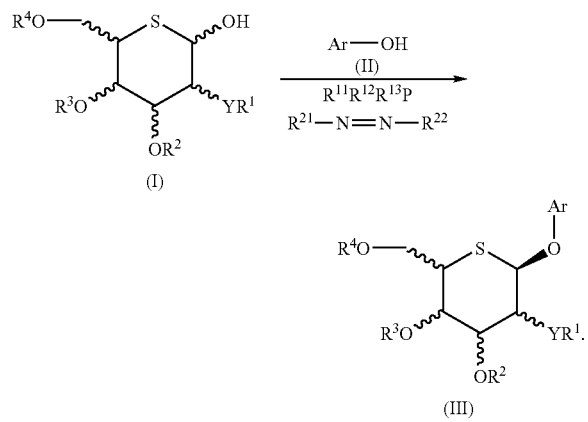

14 Claims, No Drawings

METHOD FOR SELECTIVE PREPARATION OF ARYL 5-THIO-β-D-ALDOHEXOPYRANOSIDES

This is a National Stage of Application No. PCT/JP03/10159 filed Aug. 8, 2003.

TECHNICAL FIELD

The present invention relates to a method for preparation of aryl 5-thio-β-D-aldohexopyranosides through β-selective glycosylation.

BACKGROUND ART

Chronic hyperglycemia is believed to reduce both insulin secretion and insulin sensitivity, which in turn will cause elevation of blood glucose levels and lead to exacerbation of diabetes. Drugs conventionally used as therapeutic agents for diabetes include biguanides, sulfonylureas, glycosidase inhibitors and insulin-resistance improving agents. However, adverse side effects of these drugs have been reported; for example, lactic acidosis for biguanides, hypoglycemia for sulfonylureas, and diarrhea for glycosidase inhibitors. It is therefore desirable to develop therapeutic agents for diabetes that depend on a new mechanism of action which is different from those conventionally proposed.

Phloridzin, a glucose derivative isolated from nature, has been identified as having a hypoglycemic effect by inhibiting excessive glucose reabsorption in the kidney to accelerate the glucose excretion (J. Clin. Invest., vol. 80, p. 1037, 1987; J. Clin. Invest., vol. 87, p. 1510, 1987). There have been indications that this glucose reabsorption event is mediated by sodium-dependent glucose transporter 2 (SGLT2) present at the S1 site of renal proximal tubules (J. Clin. Invest., vol. 93, p. 397, 1994).

Under these backgrounds, an increasing number of studies have been conducted to develop therapeutic agents for diabetes that depend on SGLT2 inhibition, and a large number of phloridzin derivatives have been reported (European Patent Publication No. EP0850948, International Patent Publication Nos. WO0168660, WO0116147, WO0174834, WO0174835, WO0253573, WO0268439, WO0228872, WO0268440, WO0236602, WO0288157, WO0228872, WO0244192, WO0264606, WO0311880, WO0320737, WO0300712, etc.). When administered orally, phloridzin derivatives are hydrolyzed at glycosidic linkages by the action of glycosidase present in the small intestine, thus resulting in low absorption efficiency of unchanged form and a weak hypoglycemic effect. For this reason, various attempts have been made, for example, to increase absorption efficiency by administering phloridzin derivatives in the form of prodrugs and/or to prevent digestion by synthesizing compounds replaced by carbon-carbon linkages instead of glycosidic linkages (United States Patent Nos. US20010041674, US2002137903 and US20031143, International Patent Publication Nos. WO0127128 and WO0283066, Tetrahedron Lett., vol. 41, p. 9213, 2000).

The inventors of the present invention have focused on 5-thioaldopyranoses as glucose analogs, in which the ring oxygen atom of aldopyranose is replaced by a sulfur atom. Such 5-thioaldopyranoses will show biological and chemical properties that are different from those of aldopyranoses.

However, there is no report on β-glycosidic linkage formation between aryl and 5-thioglucose in which the ring oxygen atom of glucose is replaced by a sulfur atom. Thus, there is also no report on the SGLT-inhibiting effect of 5-thio-β-D-glucopyranoside derivatives.

With the aim of developing glycosidase inhibitors, an attempt has been made to synthesize disaccharides having a 5-thiofucopyranose group or a 5-thioglucopyranose group at their nonreducing end, and it has also been reported that the trichloroacetoimidate method is effective for glycosidic linkage formation in this attempt (Tetrahedron Lett., vol. 25, p. 212, 1993, Tetrahedron Lett., vol. 33, p. 7675, 1992). In general, it has been widely known that, if a glycosyl donor has an acyl group at the 2-position, the neighboring group participation is successfully available and predominantly leads to the formation of 1,2-trans-glycosidic linkages. Interestingly, however, it has been known that, when the same approach is used in the case of 5-thioaldopyranoses, 1,2-cis-glycosides are predominantly obtained, but 1,2-trans-glycosides are not selectively obtained (Tetrahedron Assymm., vol. 5, p. 2367, 1994, J. Org. Chem., vol. 62, p. 992, 1997, Trends in Glycoscience and Glycobiology, vol. 13, p. 31, 2001). There are only two reports previously known for selective 1,2-trans-glycoside synthesis of saccharides: synthesis of 5'-thio-N-lactosamine using glycosyltransferase and UDP-5'-thiogalactose (J. Am. Chem. Soc., vol. 114, p. 5891, 1992) and an approach using benzoyl-protected 5-thioglucopyranosyl trichloroacetoimidate (Chem. Lett., p. 626, 2002).

In addition, the Mitsunobu reaction between 4-nitrophenol and 5-thio-L-arabinopyranose can be presented as an example of 5-thioglycosidic linkage formation using phenol as a glycosyl acceptor (Carbohydr. Res., vol. 311, p. 191, 1998). Alternatively, there is also a report of the Lewis acid-catalyzed condensation between thiophenol (Tetrahedron, vol. 49, p. 8977, 1993) or phenylselenol (Tetrahedron Assymm., vol. 5, p. 2367, 1994) and 5-thio-D-glucopyranose. However, these reactions would also yield a mixture of 1,2-cis- and 1,2-trans-glycosides as their reaction product. Namely, no method is known for selective chemical synthesis of aryl 1,2-trans-5-thioglycosidic linkages (β-5-thioglycosides).

DISCLOSURE OF THE INVENTION

The object of the present invention is to provide a novel method for selective preparation of aryl 5-thio-β-D-aldohexopyranoside derivatives. In particular, aryl 5-thio-β-D-glucopyranosides are expected to have a hypoglycemic effect by inhibiting the activity of sodium-dependent glucose transporter (SGLT2) involved in glucose reabsorption in the kidney to accelerate excretion of urinary sugar.

Although the inventors of the present invention have failed to achieve the above object by employing various reaction conditions known for glycosylation as found in the reference examples below, they have unexpectedly found that, when thioaldohexopyranoses are treated under Mitsunobu reaction conditions in which no β-selective glycosylation occurs in 5-thio-L-arabinoses (Carbohydr. Res., vol. 311, p. 191, 1998), such conditions cause β-selective glycosylation of thioaldohexopyranoses and enable the selective synthesis of 5-thio-β-D-aldohexopyranoside derivatives. This finding led to the completion of the present invention.

The present invention provides a method for preparing an aryl 5-thio-β-D-aldohexopyranoside derivative useful as an SGLT2 inhibitor, or a synthetic intermediate thereof, which comprises reacting a 5-thio-D-aldohexopyranose derivative with a hydroxyaryl derivative in the presence of a phosphine and an azo reagent.

More specifically, the present invention provides a method for preparing an aryl 5-thio-β-D-aldohexopyranoside derivative of Formula (III), which comprises reacting a 5-thio-D-aldohexopyranose derivative of Formula (I) with Ar-OH of Formula (II) in the presence of a phosphine represented by $PR^{11}R^{12}R^{13}$ and an azo reagent represented by $R^{21}-N=N-R^{22}$ in accordance with the following scheme:

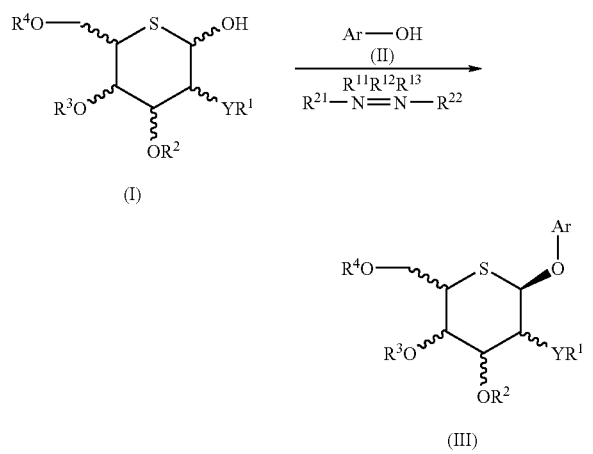

wherein
in the above Formulae (I) and (III),
the wavy lines mean containing any stereoisomer selected from the D-form, L-form and a mixture thereof,
Y represents —O— or —NH—, and
$R^1$, $R^2$, $R^3$ and $R^4$, which may be the same or different, each represent a hydrogen atom, a $C_{2-10}$ acyl group, a $C_{1-6}$ alkyl group, a $C_{7-10}$ aralkyl group, a $C_{1-6}$ alkoxy-$C_{7-10}$ aralkyl group, an allyl group, a tri($C_{1-6}$ alkyl)silyl group, a $C_{1-6}$ alkoxy-$C_{1-6}$ alkyl group or a $C_{2-6}$ alkoxycarbonyl group, or when Y represents —O—, $R^1$ and $R^2$, $R^2$ and $R^3$, or $R^3$ and $R^4$ may together form —C($R^A$)($R^B$)— wherein $R^A$ and $R^B$, which may be the same or different, each represent a hydrogen atom, a $C_{1-6}$ alkyl group or a phenyl group, in the above Formula (II), Ar represents an aryl group which may be substituted with any substituent wherein the substituent means one that does not affect the reaction, in $PR^{11}R^{12}R^{13}$, $R^{11}$ to $R^{13}$, which may be the same or different, each represent a phenyl group which may be substituted with a $C_{1-6}$ alkyl group, a pyridyl group or a $C_{1-6}$ alkyl group, and in $R^{21}-N=N-R^{22}$, $R^{21}$ and $R^{22}$, which may be the same or different, each represent a $C_{2-5}$ alkoxycarbonyl group, an N,N-di-$C_{1-4}$ alkylaminocarbonyl group or a piperidinocarbonyl group.

BEST MODE FOR CARRYING OUT THE INVENTION

The present invention preferably provides such a method as stated above, in which

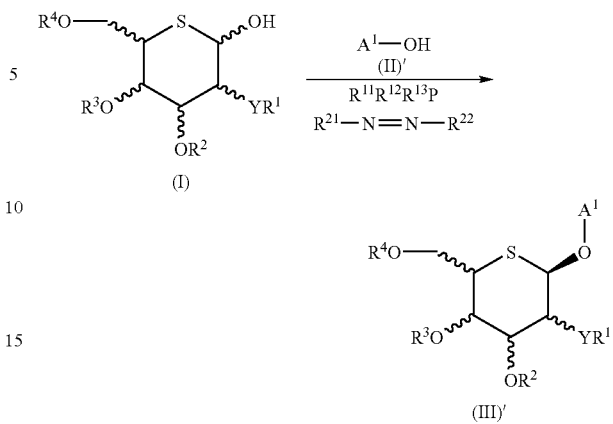

Formula (II) is represented by the above Formula (II)' and Formula (III) is represented by the above Formula (III)' (wherein Y, $R^1$, $R^2$, $R^3$ and $R^4$ are as defined above), wherein in the above Formulae (II)' and (III)', $A^1$ represents an aryl group which may be substituted with the same or different 1 to 4 substituents selected from the group consisting of:
a halogen atom;
a hydroxyl group;
—$^+NH_3$;
—$^+N(CH_3)_3$;
a $C_{1-6}$ alkyl group which may be substituted with 1 to 4 substituents selected from the group consisting of a halogen atom and a hydroxyl group;
a group represented by the formula:

—$(CH_2)_m$-Q (wherein m represents an integer of 0 to 4, and Q represents a formyl group, an amino group, a nitro group, a cyano group, a carboxyl group, a sulfonic acid group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N-($C_{1-6}$ alkyl)aminocarbonyl group, or an N,N-di($C_{1-6}$ alkyl)aminocarbonyl group;

a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group; and
a group represented by the formula:

—X-$A^2$

[wherein X represents —$(CH_2)_n$-, —CO$(CH_2)_n$-, —CH(OH)$(CH_2)_n$-, —O—$(CH_2)_n$-, —CONH$(CH_2)_n$-, —NHCO$(CH_2)_n$- (wherein n represents an integer of 0 to 3), —COCH=CH—, —S— or —NH—, and $A^2$ represents an aryl group, a heteroaryl group or a 4- to 6-membered heterocycloalkyl group, each of which may be substituted with the same or different 1 to 4 substituents selected from:

a halogen atom;

a hydroxyl group;

a $C_{1-6}$ alkyl group which may be substituted with 1 to 4 substituents selected from the group consisting of a halogen atom and a hydroxyl group;

a group represented by the formula:

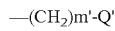

{wherein m' represents an integer of 0 to 4, and Q' represents a formyl group, an amino group, a nitro group, a cyano group, a carboxyl group, a sulfonic acid group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N-($C_{1-6}$ alkyl)aminocarbonyl group, or an N,N-di($C_{1-6}$ alkyl)aminocarbonyl group}; and a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group].

The present invention preferably provides such a method as stated above, in which

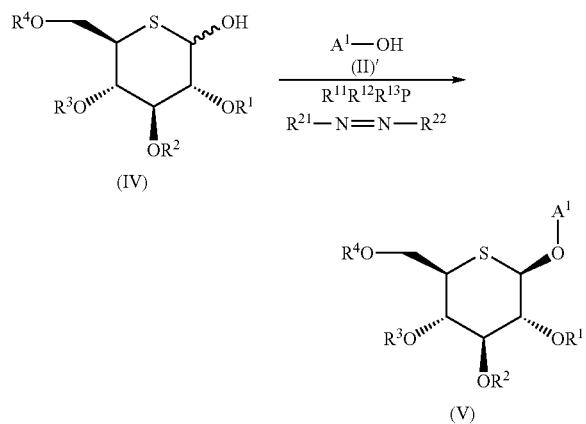

Formula (I) is represented by the above Formula (IV) (wherein $R^1$, $R^2$, $R^3$ and $R^4$ are as defined above) and Formula (III)' is represented by the above Formula (V) (wherein $A^1$, $R^1$, $R^2$, $R^3$ and $R^4$ are as defined above).

Preferably, $A^1$ represents a phenyl group substituted with —X-$A^2$ (wherein X and $A^2$ are as defined above), in which the phenyl group may be further substituted with the same or different 1 to 3 substituents selected from:

a halogen atom;

a hydroxyl group;

a $C_{1-6}$ alkyl group which may be substituted with 1 to 4 substituents selected from the group consisting of a halogen atom and a hydroxyl group;

a group represented by the formula:

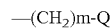

(wherein m and Q are as defined above); or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group.

More preferably, $A^1$ is represented by the following formula:

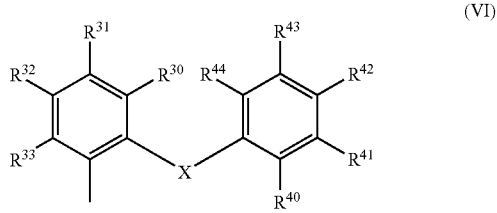

[wherein

X represents —$(CH_2)$n-, —CO$(CH_2)$n-, —CH(OH)$(CH_2)$n-, —O—$(CH_2)$n-, —CONH$(CH_2)$n-, —NHCO$(CH_2)$n- (wherein n represents an integer of 0 to 3), —COCH=CH—, —S— or —NH—, $R^{30}$, $R^{31}$, $R^{32}$ and $R^{33}$, which may be the same or different, each represent:

a hydrogen atom;

a halogen atom;

a hydroxyl group;

a $C_{1-6}$ alkyl group which may be substituted with 1 to 4 substituents selected from the group consisting of a halogen atom and a hydroxyl group;

a group represented by the formula:

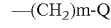

{wherein m represents an integer of 0 to 4, and Q represents a formyl group, an amino group, a nitro group, a cyano group, a carboxyl group, a sulfonic acid group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N-($C_{1-6}$ alkyl)aminocarbonyl group, or an N,N-di($C_{1-6}$ alkyl)aminocarbonyl group}; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group, and $R^{40}$, $R^{41}$, $R^{42}$, $R^{43}$ and $R^{44}$, which may be the same or different, each represent:

a hydrogen atom;

a halogen atom;

a hydroxyl group;

a $C_{1-6}$ alkyl group which may be substituted with 1 to 4 substituents selected from the group consisting of a halogen atom and a hydroxyl group;

a group represented by the formula:

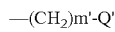
—(CH$_2$)m'-Q'

{wherein m' represents an integer of 0 to 4, and Q' represents a formyl group, an amino group, a nitro group, a cyano group, a carboxyl group, a sulfonic acid group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N-($C_{1-6}$ alkyl)aminocarbonyl group, or an N,N-di($C_{1-6}$ alkyl)aminocarbonyl group}; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group].

More preferred is such a method as stated above, in which $A^1$ is represented by the following formula:

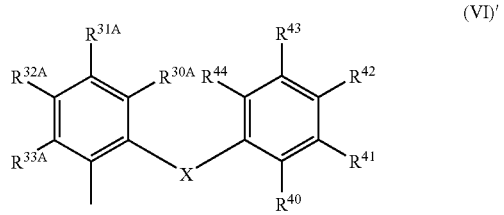

(VI)'

[wherein

X is as defined above, $R^{30A}$, $R^{31A}$, $R^{32A}$ and $R^{33A}$, which may be the same or different, each represent:

a hydrogen atom;

a halogen atom;

a hydroxyl group;

a $C_{1-6}$ alkyl group which may be substituted with 1 to 4 substituents selected from the group consisting of a halogen atom and a hydroxyl group;

a group represented by the formula:

—(CH$_2$)m$^4$-Q$^4$

{wherein m$^4$ represents an integer of 0 to 4, and Q$^4$ represents a formyl group, a carboxyl group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylsulfonyl group, or a $C_{2-10}$ acylamino group}; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, or a $C_{7-10}$ aralkylamino group, provided that each of these groups may be substituted with 1 to 4 substituents selected from the group consisting of a halogen atom, a hydroxyl group, a $C_{1-6}$ alkyl group and a $C_{1-6}$ alkoxy group, and $R^{40}$, $R^{41}$, $R^{42}$, $R^{43}$ and $R^{44}$ are as defined above].

More preferably, the compound of Formula (V) is a compound represented by the following formula:

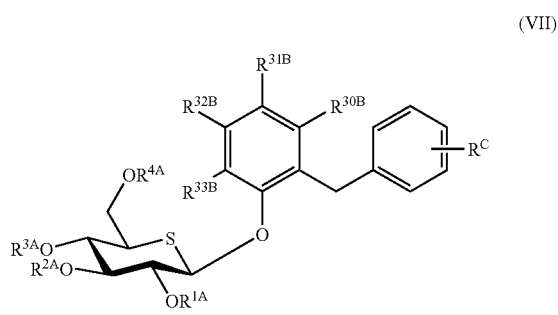

(VII)

(wherein $R^{30B}$ to $R^{33B}$, which may be the same or different, each represent a hydrogen atom, a halogen atom, a $C_{1-6}$ alkyl group, a $C_{1-6}$ alkoxy group, a $C_{1-6}$ alkoxy-$C_{1-6}$ alkoxy group, a carboxyl group, a $C_{2-6}$ alkoxycarbonyl group, a hydroxyl group or a hydroxy-$C_{1-4}$ alkyl group, $R^C$ represents a hydrogen atom, a halogen atom, a $C_{1-6}$ alkyl group, a $C_{1-6}$ alkoxy group, a hydroxy-$C_{1-4}$ alkyl group, a halogen-substituted $C_{1-6}$ alkyl group or a $C_{1-6}$ alkylthio group, $R^{4A}$ represents a hydrogen atom, a $C_{2-6}$ alkoxycarbonyl group or a $C_{2-6}$ alkanoyl group, and $R^{1A}$ to $R^{3A}$, which may be the same or different, each represent a hydrogen atom, a $C_{2-8}$ alkanoyl group or a benzoyl group).

More preferably, the compound of Formula (V) is a compound represented by the following formula:

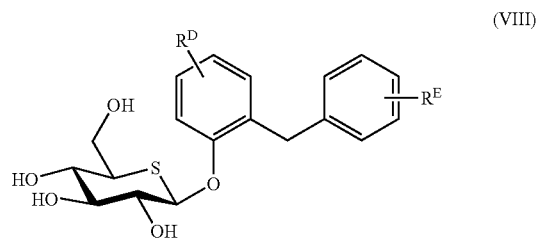

(VIII)

(wherein $R^D$ represents a hydrogen atom, a halogen atom, a $C_{1-6}$ alkyl group or a hydroxy-$C_{1-4}$ alkyl group, and $R^E$ represents a hydrogen atom, a halogen atom, a $C_{1-6}$ alkyl group, a $C_{1-6}$ alkoxy group or a hydroxy-$C_{1-4}$ alkyl group).

In the present invention, Ar (or $A^1$) is preferably an aryl group substituted with 1 to 4 electron-withdrawing groups. In a case where $A^1$ is represented by Formula (VI) (or Formula (VII) or (VIII)), at least one of $R^{30}$ to $R^{33}$ (or $R^{30A}$ to $R^{33A}$ or $R^{30B}$ to $R^{33B}$) is preferably an electron-withdrawing group.

As used herein, the term "electron-withdrawing group" refers to a substituent that is more likely to draw electrons from the atom where the substituent is attached when compared to a hydrogen atom, thus meaning that such a group draws electrons as a result of the sum of substituent effects including an inductive effect and a mesomeric effect (or a resonance effect).

Representative examples include a formyl group, a nitro group, a cyano group, a carboxyl group, a sulfonic acid group, $-^+NH_3$, $-^+N(CH_3)_3$, $-CF_3$, $-CCl_3$, $-COCH_3$, $-CO_2CH_3$, $-CO_2C_2H_5$, $-COPh$, $-SO_2CH_3$ and a halogen atom.

Preferred is $-CF_3$, $-CCl_3$, $-COCH_3$, $-CO_2CH_3$, $-CO_2C_2H_5$, $-COPh$ (wherein Ph denotes a phenyl group) or a halogen atom.

The substitution position is preferably the ortho and/or para position relative to the OH group of an aryl alcohol.

When a compound substituted with an electron-withdrawing group(s) is used as an aryl alcohol to be glycosylated, such a compound ensures a high yield of glycosylation reaction.

This is because the acidity of an aryl alcohol to be glycosylated would heavily contribute to the reaction yield in this reaction.

Thus, an aryl group to be glycosylated may be introduced with an electron-withdrawing group(s) and then glycosylated, followed by processes such as catalytic hydrogenation, hydrolysis or decarboxylation to remove the electron-withdrawing group(s), or alternatively, followed by techniques well known to those skilled in the art (e.g., reduction) to convert each electron-withdrawing group into any other substituent, thus providing an aryl 5-thio-β-D-aldohexopyranoside derivative of interest in high yield.

For example, in a case where an aryl alcohol having a halogen atom (e.g., a bromine atom) which is introduced as an electron-withdrawing group is used for glycosylation, the halogen atom can be removed by catalytic hydrogenation after glycosylation.

In a "phosphine represented by $PR^{11}R^{12}R^{13}$" as used in this reaction, $R^{11}$ to $R^{13}$ may be the same or different and each represents a phenyl group which may be substituted with a $C_{1-6}$ alkyl group (e.g., a phenyl group, a tolyl group), a pyridyl group, or a $C_{1-6}$ alkyl group (e.g., a methyl group, a n-butyl group, a t-butyl group). Preferred examples of phosphines include triphenylphosphine, tri-n-butylphosphine, tri-t-butylphosphine, tritolylphosphine and diphenyl-2-pyridylphosphine. Among them, preferred are triphenylphosphine and diphenyl-2-pyridylphosphine, and more preferred is triphenylphosphine.

In an "azo reagent represented by $R^{21}-N=N-R^{22}$," $R^{21}$ and $R^{22}$ may be the same or different and each represents a $C_{2-5}$ alkoxycarbonyl group, an N,N-di-$C_{1-4}$ alkylaminocarbonyl group, or a piperidinocarbonyl group. Examples of azo reagents preferred for use include diethyl azodicarboxylate, diisopropyl azodicarboxylate and di-tert-butyl azodicarboxylate, as well as 1,1'-azobis(N,N-dimethylformamide) and 1,1'-(azodicarbonyl)dipiperidine. Among them, diethyl azodicarboxylate (DEAD), diisopropyl azodicarboxylate and the like are particularly listed.

Solvents available for use in this reaction include tetrahydrofuran, dioxane, toluene, methylene chloride, chloroform, acetonitrile, ethyl acetate, dimethyl sulfoxide and N,N-dimethylformamide, with tetrahydrofuran and toluene being preferred and with toluene being more preferred.

The reaction temperature preferably ranges from $-20°$ C. to room temperature.

Starting materials used in this reaction may be either commercially available or synthesized as follows.

When 5-thio-D-glucopyranose (IV) is given as an example of the 5-thio-D-aldohexopyranose derivative of Formula (I), this derivative can be prepared as shown below, by way of example.

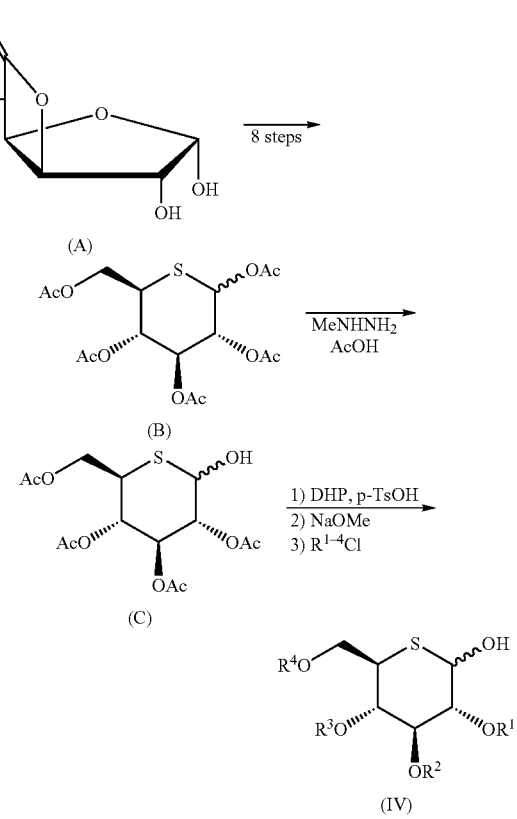

The penta-O-acetate derivative (B) (Tetrahedron Lett., vol. 22, p. 5061, 1981; J. Org. Chem., vol. 31, p. 1514, 1966) can be synthesized via 8 steps from D-glucofurano-3,6-lactone (A).

Next, Compound (B) may be treated in an appropriate solvent (e.g., DMF, THF, methanol, ethanol) using hydrazine acetate (Tetrahedron, Lett., vol. 33, p. 7675, 1992) or benzylamine, preferably a 1:1 mixture of methylhydrazine and acetic acid, to effect selective deprotection of the 1-position acetyl group, thereby preparing Compound (C).

The reaction temperature ranges from room temperature to 80° C., while the reaction time ranges from 20 minutes to 24 hours.

After the 1-position hydroxyl group of Compound (C) is protected (e.g., with a tetrahydropyranyl group), the compound may be deprotected to remove the acetyl groups and treated with, e.g., a $C_{2-6}$ alkanoyl chloride or benzoyl chloride under basic conditions, thereby giving the 5-thio-D-glucopyranose derivative (IV) (wherein $R^1$, $R^2$, $R^3$ and $R^4$, which may be the same or different, each represent a $C_{2-6}$ alkanoyl group or a benzoyl group) (Chem. Lett., p. 626, 2002).

In a case where Ar-OH of Formula (II) and $A^1$-OH of Formula (II)', each of which corresponds to the aglycon, are phenol derivatives, they can be synthesized by reference to the following official gazettes: International Patent Publication Nos. WO0168660, WO0174834, WO0174835, WO0228872, WO0244192, WO0264606 and WO0311880.

A compound, in which $A^1$ in $A^1$-OH is represented by Formula (VI) and X is $-CH_2-$, can also be prepared though condensation between a phenol derivative and a benzyl alcohol derivative under acidic conditions.

An acid available for use in the condensation may be, for example, methanesulfonic acid or p-toluenesulfonic acid. If a solvent is used, a high-boiling solvent such as nitrobenzene is preferred. The reaction temperature ranges from 100° C. to 200° C., while the reaction time ranges from 10 minutes to 150 minutes.

After the completion of this reaction, the resulting compound may further be deprotected to remove the protecting groups of sugar hydroxyl groups, if necessary.

The deprotection may be accomplished by using a base such as sodium methoxide, sodium hydroxide, lithium hydroxide, potassium carbonate, cesium carbonate or triethylamine. Solvents suitable for the reaction include methanol, ethanol and aqueous methanol.

The terms and phrases used herein are defined as follows (in the definitions, the designation "$C_{x-y}$" is intended to mean a group containing x to y carbon atoms).

The term "5-thio-D-aldohexopyranose derivative" is intended to mean a sugar analog in which the 5-position oxygen atom (i.e., the ring oxygen atom) of aldopyranose is replaced by a sulfur atom. Examples include 5-thio-D-glucopyranose, 5-thio-D-galactopyranose (Carbohydr. Res., vol. 76, p. 165, 1979), 5-thio-D-mannopyranose (J. Carbohydr. Chem., vol. 8, p. 753, 1989), 2-deoxy-2-amino-5-thio-D-glucopyranose, 2-deoxy-2-amino-5-thio-D-galactopyranose (Bioorg. Med. Chem. Lett., vol. 7, p. 2523, 1997), 5-thio-D-allopyranose, 5-thio-D-altropyranose, 5-thio-D-idopyranose and 5-thio-D-talopyranose, with a 5-thio-D-glucopyranose derivative being more preferred.

In Formula (I), $R^1$, $R^2$, $R^3$ and $R^4$ each represent a hydrogen atom, a $C_{2-10}$ acyl group (e.g., an acetyl group, a pivaloyl group, a benzoyl group), a $C_{1-6}$ alkyl group (e.g., a methyl group, an ethyl group), a $C_{7-10}$ aralkyl group (e.g., a benzyl group), a $C_{1-6}$ alkoxy-$C_{7-10}$ aralkyl group (e.g., a p-methoxybenzyl group), an allyl group, a tri($C_{1-6}$ alkyl)silyl group (e.g., a trimethylsilyl group, a triethylsilyl group, a t-butyldimethylsilyl group) or a $C_{1-6}$ alkoxy-$C_{1-6}$ alkyl group (e.g., a methoxymethyl group).

In a case where Y is —O—, $R^1$ and $R^2$, $R^2$ and $R^3$, or $R^3$ and $R^4$ may together form —C($R^A$)($R^B$)— (wherein $R^A$ and $R^B$, which may be the same or different, each represent a hydrogen atom, a $C_{1-6}$ alkyl group or a phenyl group), as exemplified by an acetal group, an isopropylidene group and a benzylidene group.

The term "aryl group" encompasses a phenyl group and a naphthyl group (including a 1-naphthyl group and a 2-naphthyl group), preferably refers to a phenyl group.

The term "$C_{2-10}$ acyl group" is intended to mean a linear or branched aliphatic acyl group (preferably a $C_{2-6}$ alkanoyl group) or an aromatic acyl group, which contains 2 to 10 carbon atoms. Examples include an acetyl group, a propionyl group, a pivaloyl group, a butyryl group, an isobutyryl group, a valeryl group and a benzoyl group, with an acetyl group being preferred.

The term "$C_{1-6}$ alkyl group" is intended to mean a linear or branched alkyl group containing 1 to 6 carbon atoms. Examples include a methyl group, an ethyl group, a n-propyl group, an isopropyl group, a n-butyl group, an isobutyl group, a tert-butyl group, a sec-butyl group, a n-pentyl group, a tert-amyl group, a 3-methylbutyl group and a neopentyl group.

The term "$C_{7-10}$ aralkyl group" refers to an aryl alkyl group containing 7 to 10 carbon atoms. Examples include a benzyl group and a phenylethyl group.

The term "$C_{1-6}$ alkoxy group" is intended to mean a linear or branched alkoxy group containing 1 to 6 carbon atoms. Preferred are $C_{1-4}$ alkoxy groups including a methoxy group, an ethoxy group, a propoxy group, an isopropoxy group, a n-butoxy group, an isobutoxy group and a tert-butoxy group.

The term "$C_{1-6}$ alkoxy-$C_{7-10}$ aralkyl group" is intended to mean a structure composed of a $C_{1-6}$ alkoxy group and a $C_{7-10}$ aralkyl group. Examples include a p-methoxybenzyl group.

The term "tri($C_{1-6}$ alkyl)silyl group" refers to a silyl group whose hydrogen atoms are replaced by three $C_{1-6}$ alkyl groups. Examples include a trimethylsilyl group, a triethylsilyl group and a t-butyldimethylsilyl group.

The term "$C_{1-6}$ alkoxy-$C_{1-6}$ alkyl group" is intended to mean a structure composed of a $C_{1-6}$ alkoxy group and a $C_{1-6}$ alkyl group. Examples include a methoxymethyl group.

The term "halogen atom" encompasses a fluorine atom, a chlorine atom, a bromine atom, an iodine atom and the like.

The phrase "$C_{1-6}$ alkyl group substituted with 1 to 4 halogen atoms" refers to a $C_{1-6}$ alkyl group whose hydrogen atoms are replaced by 1 to 4 halogen atoms (preferably fluorine atoms). Examples include a trifluoromethyl group, a 1,1,1-trifluoroethyl group, a 1,1,1-trifluoropropyl group and a 1,1,1-trifluorobutyl group, with a trifluoromethyl group and a 1,1,1-trifluoroethyl group being preferred.

The phrase "$C_{1-6}$ alkyl group substituted with 1 to 4 hydroxyl groups" refers to an alkyl group whose hydrogen atoms are replaced by 1 to 4 hydroxyl groups. Preferred is a hydroxy-$C_{1-6}$ alkyl group (i.e., a $C_{1-6}$ alkyl group substituted with one hydroxyl group), and more preferred is a hydroxy-$C_{1-4}$ alkyl group. Examples include a hydroxymethyl group, a hydroxyethyl group (e.g., a 1-hydroxyethyl group), a hydroxypropyl group and a hydroxybutyl group.

The phrase "$C_{1-6}$ alkoxy group substituted with 1 to 4 halogen atoms" refers to an alkoxy group whose hydrogen atoms are replaced by halogen atoms. Examples include a trifluoromethoxy group, a 1,1,1-trifluoroethoxy group, a 1,1,1-trifluoropropoxy group and a 1,1,1-trifluorobutoxy group, with a trifluoromethoxy group and a 1,1,1-trifluoroethoxy group being preferred.

The term "$C_{1-6}$ alkoxy-$C_{1-6}$ alkoxy group" is intended to mean, for example, a methoxymethoxy group.

The term "$C_{2-10}$ acyloxy group" is intended to mean a structure composed of a $C_{2-10}$ acyl group and a —O— moiety. Preferred are a $C_{2-6}$ alkanoyloxy group (e.g., an acetyloxy group) and a benzoyloxy group.

The term "$C_{2-6}$ alkoxycarbonyl group" is intended to mean a structure composed of a linear or branched $C_{1-5}$ alkoxy group and a carbonyl group. Preferred are $C_{2-1}$ alkoxycarbonyl groups including a methoxycarbonyl group, an ethoxycarbonyl group, a propoxycarbonyl group, an isopropoxycarbonyl group and a butoxycarbonyl group. Among them, a methoxycarbonyl group is preferred.

The term "$C_{1-6}$ alkylthio group" is intended to mean a structure composed of a linear or branched $C_{1-6}$ alkyl group and one thio group (—S—), preferably refers to a $C_{1-4}$ alkylthio group. Examples of a $C_{1-6}$ alkylthio group include a methylthio group, an ethylthio group and a propylthio group.

The term "$C_{1-6}$ alkylsulfinyl group" is intended to mean a structure composed of a $C_{1-6}$ alkyl group and a sulfinyl group (—SO—). Preferred are a methanesulfinyl group and an ethanesulfinyl group.

The term "$C_{1-6}$ alkylsulfonyl group" is intended to mean a structure composed of a $C_{1-6}$ alkyl group and a sulfonyl group (—$SO_2$—). Preferred are a methanesulfonyl group and an ethanesulfonyl group.

The term "$C_{2-10}$ acylamino group" is intended to mean a structure composed of a $C_{2-10}$ acyl group and an amino group. Preferred is an acetylamino group.

The term "$C_{1-6}$ alkylsulfonylamino group" is intended to mean a structure composed of a $C_{1-6}$ alkylsulfonyl group and an amino group. Examples include a methanesulfonylamino group and an ethanesulfonylamino group.

The term "$C_{1-6}$ alkylamino group" is intended to mean a structure composed of a $C_{1-6}$ alkyl group and an amino group. Examples include a methylamino group and an ethylamino group.

The term "N,N-di($C_{1-6}$ alkyl)amino group" is intended to mean a structure composed of two $C_{1-6}$ alkyl groups and an amino group. Examples include a dimethylamino group and a diethylamino group.

The term "N-($C_{1-6}$ alkyl)aminocarbonyl group" is intended to mean a structure composed of an N-($C_{1-6}$ alkyl)amino group and a carbonyl group. Preferred are N-($C_{1-4}$ alkyl)aminocarbonyl groups including an N-methylaminocarbonyl group.

The term "N,N-di($C_{1-6}$ alkyl)aminocarbonyl group" is intended to mean a structure composed of an N,N-di($C_{1-6}$ alkyl)amino group and a carbonyl group. Preferred are N,N-di($C_{1-4}$ alkyl)aminocarbonyl groups including an N,N-dimethylaminocarbonyl group.

Examples of the groups —$(CH_2)m$-Q, —$(CH_2)m'$-Q' and —$(CH_2)m^A$-$Q^A$ wherein m, m' and $m^A$ each represent an integer of 1 or more will be provided below.

In a case where Q, Q' and $Q^A$ each represent a $C_{1-6}$ alkoxy group, examples include a methoxymethyl group.

In a case where Q and Q' each represent an amino group, examples include an aminomethyl group.

In a case where Q, Q' and $Q^A$ each represent a $C_{2-10}$ acyloxy group, examples include an acetyloxymethyl group and a benzoyloxyethyl group.

In a case where Q, Q' and $Q^A$ each represent a $C_{2-10}$ acylamino group, examples include an acetylaminomethyl group.

In a case where Q and Q' each represent an N,N-di($C_{1-6}$ alkyl)amino group, examples include an N,N-dimethylaminomethyl group.

The term "$C_{3-7}$ cycloalkyl group" is intended to mean a cyclic alkyl group containing 3 to 7 carbon atoms. Examples include a cyclopropyl group, a cyclobutyl group, a cyclopentyl group and a cyclohexyl group, with a cyclopropyl group being preferred.

The term "aryloxy group" is intended to mean a structure composed of an aryl group and a —O— moiety. Examples include a phenoxy group and a naphthoxy group.

The term "$C_{3-7}$ cycloalkyloxy group" is intended to mean a structure composed of a $C_{3-7}$ cycloalkyl group and a —O— moiety. Examples include a cyclopropyloxy group and a cyclopentyloxy group.

The term "$C_{7-10}$ aralkyloxy group" is intended to mean a structure composed of a $C_{7-10}$ aralkyl group and a —O— moiety. Examples include a benzyloxy group and a phenylethyloxy group.

The term "$C_{7-10}$ aralkylamino group" is intended to mean a structure composed of a $C_{7-10}$ aralkyl group and an —NH— moiety. Examples include a benzylamino group and a phenylethylamino group.

The term "heteroaryl group" encompasses a pyridyl group, a thiazolyl group, an isothiazolyl group, a thiadiazolyl group, a pyrazolyl group, an imidazolyl group, a furyl group (including a 2-furyl group and a 3-furyl group), a thienyl group (including a 2-thienyl group and a 3-thienyl group), an oxazolyl group, an isoxazolyl group, a pyrrolyl group (including a 1-pyrrolyl group, a 2-pyrrolyl group and a 3-pyrrolyl group, preferably a 1-pyrrolyl group), a triazolyl group, a pyrimidinyl group, a pyrazinyl group, a pyridazinyl group, a quinolinyl group, an isoquinolinyl group, a benzofuranyl group, a benzothiazolyl group and a benzothienyl group.

The term "4- to 6-membered heterocycloalkyl group" refers to a 4- to 6-membered heterocycloalkyl group containing at least one heteroatom (oxygen atom, nitrogen atom or sulfur atom) in the ring. For example, such a group may be a cyclic amino group that contains one or more nitrogen atoms in the ring and may further contain one or more oxygen atoms and/or sulfur atoms. Examples include a morpholino group, a piperidinyl group, a piperazinyl group and a 1-pyrrolidinyl group.

In relation to examples of a heteroaryl group substituted with 1 to 4 substituents, explanation will now be given of a case where the substituents are each a $C_{1-6}$ alkyl group.

A "thiazolyl group substituted with a $C_{1-6}$ alkyl group(s)" is intended to mean a thiazolyl group in which at least one hydrogen atom on the ring is replaced by a $C_{1-6}$ alkyl group, preferably by a $C_{1-4}$ alkyl group, and more preferably by a methyl group. Examples include a 4-methylthiazol-2-yl group.

A "pyridyl group substituted with a $C_{1-6}$ alkyl group(s)" is intended to mean a pyridyl group in which at least one hydrogen atom on the ring is replaced by a $C_{1-6}$ alkyl group, preferably by a $C_{1-4}$ alkyl group, and more preferably by a methyl group. Examples include a 2-methylpyridin-5-yl group.

A "pyrazolyl group substituted with a $C_{1-6}$ alkyl group(s)" is intended to mean a pyrazolyl group in which at least one hydrogen atom on the ring is replaced by a $C_{1-6}$ alkyl group, preferably by a $C_{1-4}$ alkyl group, and more preferably by a methyl group or an ethyl group. Examples include a 1-methylpyrazol-4-yl group and a 1-ethylpyrazol-4-yl group.

A "pyrrolyl group substituted with a $C_{1-6}$ alkyl group(s)" is intended to mean a pyrrolyl group in which at least one hydrogen atom on the ring is replaced by a $C_{1-6}$ alkyl group, preferably by a $C_{1-4}$ alkyl group, and more preferably by a methyl group. Examples include a 1-methylpyrrolyl group.

To mention examples of a heterocycloalkyl group substituted with 1 to 4 substituents, explanation will be given of a case where the substituents are each a $C_{1-6}$ alkyl group.

A "4-$C_{1-6}$ alkylpiperazinyl group" is intended to mean a 1-piperazinyl group in which a hydrogen atom present on one nitrogen atom is replaced by a $C_{1-6}$ alkyl group. Examples include a 4-methylpiperazin-1-yl group and a 4-ethylpiperazin-1-yl group.

Preferred embodiments for the compound of the present invention will be provided below.

Preferred examples of X are: —$(CH_2)n$- (wherein n is an integer of 0 to 3), —$CO(CH_2)n$- (wherein n is an integer of 0 to 3) and —$CONH(CH_2)n$- (wherein n is an integer of 0 to 3).

More preferred examples of X are: —$CH_2$— and —CO$(CH_2)n$- (wherein n is an integer of 0 to 2).

$R^{40}$, $R^{41}$, $R^{42}$, $R^{43}$ and $R^{44}$ in Formulae (VI) and (VI)' may be the same or different and each preferably represents:

a hydrogen atom;

a halogen atom;

a hydroxyl group;

a $C_{1-6}$ alkyl group which may be substituted with 1 to 4 substituents selected from the group consisting of a halogen atom and a hydroxyl group;

a group represented by the formula:

—$(CH_2)m'$-Q'

{wherein m' represents an integer of 0 to 4, and Q' represents a nitro group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, a $C_{2-10}$ acylamino group, a $C_{1-6}$ alkylsulfonylamino group, a carbamoyl group, an N,N-di($C_{1-6}$ alkyl)amino group, or an N,N-di($C_{1-6}$ alkyl)aminocarbonyl group}; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group.

More preferably, $R^{40}$, $R^{41}$, $R^{42}$, $R^{43}$ and $R^{44}$ may be the same or different and each represents:

a hydrogen atom;

a halogen atom;

a hydroxyl group;

a $C_{1-6}$ alkyl group which may be substituted with 1 to 4 substituents selected from the group consisting of a halogen atom and a hydroxyl group;

a group represented by the formula:

—(CH$_2$)m'-Q'

{wherein m' represents an integer of 0 to 4, and Q' represents a nitro group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{2-10}$ acylamino group, a $C_{1-6}$ alkylsulfonylamino group, or a carbamoyl group}; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, or a heteroaryl group, provided that each of these groups may be substituted with 1 to 4 substituents selected from the group consisting of a halogen atom, a hydroxyl group, a $C_{1-6}$ alkyl group and a $C_{1-6}$ alkoxy group.

In relation to the 5-thio-β-D-glycosylation reaction in the present invention, explanation will be given with reference to the following embodiments shown in Schemes 1 and 2 below.

It is also explained that the reaction of the present invention is a superior β-selective reaction when compared to 5-thio-glycosylation reactions performed under various conditions known for glycosylation shown in the reference examples below.

When 2,3,4,6-tetra-O-acetyl-5-thio-D-glucopyranose (7) and 2-(4-ethylbenzyl)phenol (9) were reacted in the presence of triphenylphosphine and diethyl azodicarboxylate (DEAD), 2'-(4'-ethylbenzyl)phenyl 2,3,4,6-tetra-O-acetyl-5-thio-β-D-glucopyranoside (10) could be selectively obtained in a yield of 8–10%.

Scheme 1

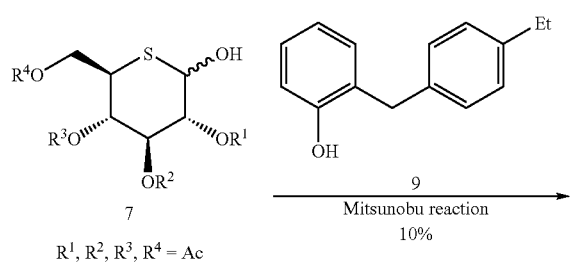

$R^1, R^2, R^3, R^4 = Ac$

-continued

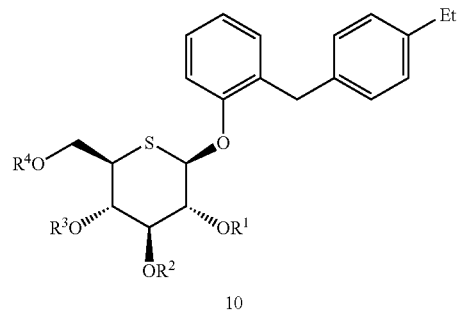

10

$R^1, R^2, R^3, R^4 = Ac$

Even when $R^1$, $R^2$, $R^3$ and $R^4$ were other substituents (e.g., benzoyl groups or pivaloyl groups), products of interest could also be obtained.

In the case of using an aryl alcohol substituted with an electron-withdrawing group(s) (e.g., a halogen atom, a nitro group), the yield could be dramatically improved.

Scheme 2

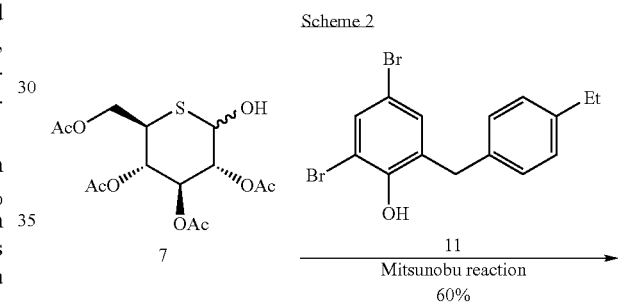

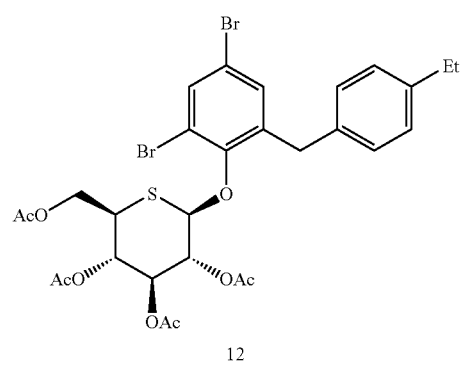

12

For example, when using phenol 11 which was modified to have electron-withdrawing groups, such as bromine atoms, introduced onto the phenol ring of 2-(4-ethylbenzyl)phenol, the yield of glycosylation reaction could be increased to 50–60% (Example 2). It should be noted that the electron-withdrawing groups on the benzene ring may be removed after the Mitsunobu reaction by treating Compound 12 by catalytic hydrogenation or the like to remove the halogen atoms, thereby giving Compound 10.

In contrast to this, 5-thio-glycosylation reactions were performed under known glycosylation conditions using the following thiosugar derivatives, as shown below.

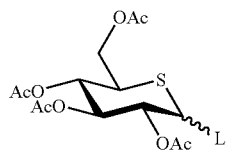

L = leaving group
1 L = Br
2 L = OCNHCCl₃
3 L = OPOEt₂
4 L = OAc
5 L = OTMS
6 L = OTs
7 L = OH

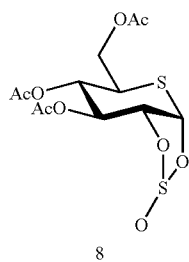

8

To synthesize an aryl β-D-glucopyranoside, a reaction is employed that uses D-glycopyranosyl bromide as a glycosyl donor and potassium carbonate or the like as a base, as well as using a phase-transfer catalyst (Synth. Commun., vol. 20, p. 2095, 1990, Synth. Commun., vol. 29, p. 2775, 1999). This approach was adapted to condensation between 5-thio-β-D-glucopyranosyl bromide (1) (Tetrahedron, vol. 49, p. 8977, 1993) and 2-(4-ethylbenzyl)phenol, but it failed to provide a product of interest and ended in allowing the collection of starting materials (see Reference Example 1).

2,3,4,6-Tetra-O-acetyl-5-thio-β-D-glucopyranosyl trichloroacetoimidate (2), which has been most commonly used for glycosylation, was used to effect glycosylation of 2-(4-ethylbenzyl)phenol in the presence of TMSOTf as a Lewis acid catalyst. However, it was impossible to obtain the desired 5-thio-β-D-glucopyranoside [2-(4-ethylbenzyl)phenyl 2,3,4,6-tetra-O-acetyl-5-thio-β-D-glucopyranoside] (10) (see Reference Example 2).

A combination of glucosyl phosphate and an insoluble acid catalyst (montmorillonite K-10) was tested because such a combination was reported to be advantageous for β-O-glucoside synthesis (Tetrahedron Lett., vol. 43, p. 847, 2002). Diethyl 2,3,4,6-tetra-O-acetyl-5-thio-α/β-D-glucopyranosyl phosphate (3) and K-10 were used to effect glycosylation of 2-(4-ethylbenzyl)phenol. However, it was completely impossible to obtain a product of interest. In addition to this, the same reaction was tested for other Lewis acid catalysts such as Yb(OTf)₂, Sn(OTf)₂ and Sc(OTf)₃, but the attempt failed to provide any product of interest (see Reference Example 4).

Another examination was made under the same reaction conditions as used for glycosylation in which a 1-O-acetylated glycosyl donor (which has been used in many reports of glycosylation reactions) was activated with a Lewis acid (Chem. Ber., vol. 66, p. 378, 1933, Can. J. Chem., vol. 31, p. 528, 1953, J. Carbohydr. Res., vol. 59, p. 261, 1977, Carbohyde. Res., vol. 72, p. C15, 1979, Carbohyde. Res., vol. 114, p. 328, 1983, Carbohyde. Res., vol. 93, p. C6, 1981, Chem. Lett., p. 145, 1989, Chem. Lett., p. 533, 1991, Chem. Lett., p. 985, 1991). Various Lewis acids found in the above documents were used to effect glycosylation of 2-(4-ethylbenzyl)phenol with 1,2,3,4,6-penta-O-acetyl-5-thio-D-glucopyranose (4), but the attempts failed to provide any product of interest (see Reference Example 5).

Tietze et al. have reported a method for selective preparation of phenyl β-D-glucopyranoside using 1-O-trimethylsilyl glucose and phenyltrimethylsilyl ether in the presence of TMSOTf as a catalyst (Tetrahedron Lett., vol. 23, p. 4661, 1982). 2,3,4,6-Tetra-O-acetyl-1-O-trimethylsilyl-5-thio-D-glucopyranose (5) and 2-(4-ethylbenzyl)phenyltrimethylsilyl ether were prepared and provided for the reaction, but it was completely impossible to obtain a product of interest (see Reference Example 6).

Based on the consideration that the kinetically-controlled SN₂ substitution is advantageous for 5-thio-β-D-glucopyranoside formation, the reaction between 1-O-tosyl derivative (6) or 1,2-cyclic sulfite (8) and 2-(4-ethylbenzyl)phenol was attempted under the same reaction conditions as used for glycosylation through a 1-O-sulfonyl derivative or a 1,2-cyclic sulfite (Tetrahedron Lett., vol. 35, p. 6279, 1994), but it was impossible to obtain a product of interest (see Reference Examples 7 and 8).

Another attempt was made to directly treat the 1-position hydroxyl group by dehydration condensation. 2,3,4,6-Tetra-O-acetyl-5-thio-D-glucopyranose (7) and 2-(4-ethylbenzyl) phenol were heated at reflux in the presence of montmorillonite K-10. The attempt failed to provide the desired glucoside, and a thiophene derivative (J. Chem. Soc. Perkin Trans. 1, p. 2763, 1990) was obtained as a major product (see Reference Example 9).

Likewise, the reaction using a diphosphonium salt effective for ribofuranoside synthesis (Chem. Lett., p. 1143, 1990) was also adapted to glycosylation between (7) and 2-(4-ethylbenzyl)phenol, but it ended in allowing the collection of starting materials.

Reference Example 1

2,3,4,6-Tetra-O-acetyl-5-thio-β-D-glucopyranosyl bromide (1) (Tetrahedron, vol. 49, p. 8977, 1993), 2-(4-ethylbenzyl)phenol (9), potassium carbonate and benzyl tri-n-butylammonium chloride were mixed in chloroform and heated at 60° C. However, it was completely impossible to obtain a glycosylation product. 2-(4-Ethylbenzyl)phenyl acetate was obtained as a by-product.

Reference Example 2

TMSOTf was added at −78° C. to a mixture of 2,3,4,6-tetra-O-acetyl-5-thio-β-D-glucopyranosyl trichloroacetoimidate (2), 2-(4-ethylbenzyl)phenol (9), MS4A and CH₂Cl₂. Instead of the desired 5-thio-β-D-glucopyranoside (10), this reaction provided an aryl α-C-glucoside (16) (yield 30%).

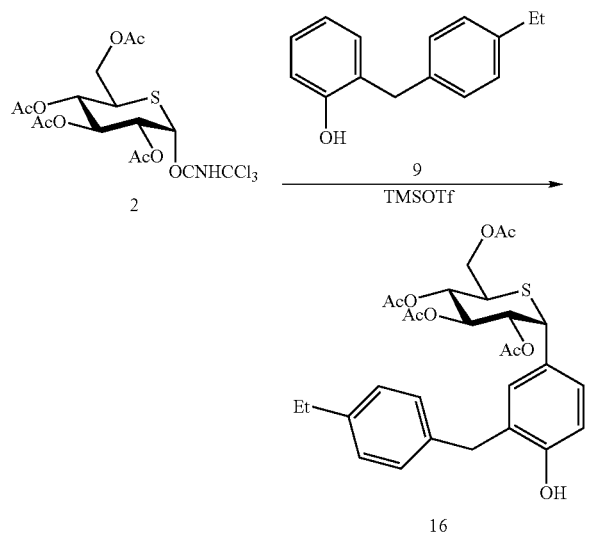

Reference Example 3

BF$_3$·Et$_2$O was added at −78° C. to a mixture of 2,3,4,6-tetra-O-benzoyl-5-thio-β-D-glucopyranosyl trichloroacetoimidate (17), 2-(4-ethylbenzyl)phenol (9), MS4A and CH$_2$Cl$_2$. This reaction provided the desired 5-thio-β-D-glucopyranoside (18) and 5-thio-α-D-glucopyranoside (19) in yields of 16% and 18%, respectively, along with the major product aryl α-C-glucoside (20) (yield 57%).

Reference Example 4

A mixture of diethyl 2,3,4,6-tetra-O-acetyl-5-thio-α/β-D-glucopyranosyl phosphite (3), 2-(4-ethylbenzyl)phenol (9) and montmorillonite K-10 was reacted in CH$_3$CN at −20° C. However, this reaction failed to produce a product of interest (10) and only provided a very small amount of the aryl α-C-glucoside (16), as in the case of the imidate method.

Reference Example 5

1,2,3,4,6-Penta-O-acetyl-5-thio-D-glucopyranose (4), 2-(4-ethylbenzyl)phenol (9) and a Lewis acid (K-10, Yb(OTf)$_3$, Yb(OTf)$_3$, Sc(OTf)$_2$ or SnCl$_4$) were reacted in a solvent (DMF, DMSO or toluene). However, it was impossible to obtain a product of interest (10) in either case.

Reference Example 6

TMSOTf was added at 0° C. to a mixture of 2,3,4,6-tetra-O-acetyl-1-O-trimethylsilyl-5-thio-D-glucopyranose (5), 2-(4-ethylbenzyl)phenyltrimethylsilyl ether, MS4A and CH$_2$Cl$_2$. Instead of a product of interest (10), this reaction provided 2,3,4,6-tetra-O-acetyl-5-thio-D-glucopyranose (7) as a by-product in a yield of 54%.

Reference Example 7

A 1-O-sulfonyl derivative was prepared from 2,3,4,6-tetra-O-acetyl-5-thio-D-glucopyranose (7) and provided for reaction with 2-(4-ethylbenzyl)phenol (9), but the attempt failed to provide a product of interest (10).

Reference Example 8

1,2-Cyclic sulfite (8) was prepared from 3,4,6-tri-O-acetyl-5-thio-D-glucopyranose and provided for reaction

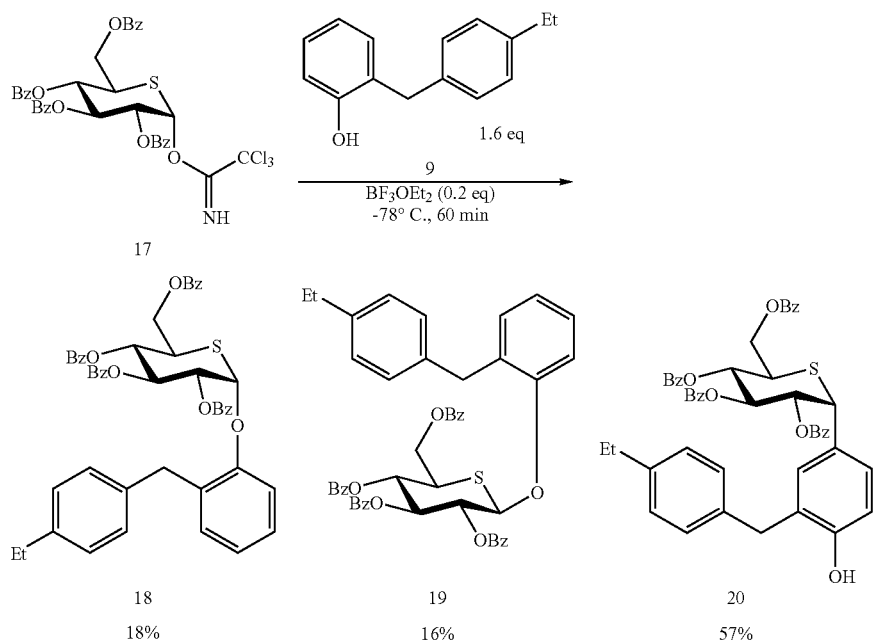

with 2-(4-ethylbenzyl)phenol (9), but the attempt failed to provide a product of interest (10).

Reference Example 9

2,3,4,6-Tetra-O-acetyl-5-thio-D-glucopyranose (7), 2-(4-ethylbenzyl)phenol (9) and montmorillonite K-10 were heated at reflux in a solvent ($CH_2Cl_2$, $CCl_4$, $ClCH_2CH_2Cl$, $CHCl_2CHCl_2$, $CCl_2=CCl_2$, toluene, chlorobenzene, o-dichlorobenzene or trifluoromethylbenzene). This reaction failed to produce a product of interest (10), and a thiophene derivative (J. Chem. Soc. Perkin Trans. 1, p. 2763, 1990) was obtained as a major product.

PREPARATION EXAMPLES

Starting materials used in the preparation method of the present invention will be illustrated with reference to the following Preparation Examples 1 to 7.

Preparation Example 1

Preparation of 4-chloro-2-(4-ethylbenzyl)phenol

A mixture of 4-chlorophenol (2.0 g, 15.6 mmol), 4-ethylbenzylalcohol (2.12 g, 15.6 mmol) and methanesulfonic acid (80 mg, 0.83 mmol) was heated and stirred at 160° C. for 25 minutes. The reaction mixture was purified by silica gel column chromatography (hexane:ethyl acetate=9:1) to give 4-chloro-2-(4-ethylbenzyl)phenol (1.78 g, 46%) as a light-yellow oil.

Preparation Example 2

Preparation of methyl 3-(4-ethylbenzyl)-4-hydroxybenzoate

To a mixture of methyl 4-hydroxybenzoate (20 g, 131 mmol) and methanesulfonic acid (80 mL), hexamethylenetetramine (20 g, 144 mmol) was added in small portions at room temperature. After stirring at 100° C. for 3.5 hours, concentrated hydrochloric acid (10 mL) and water (300 mL) were added. The reaction mixture was extracted twice with ethyl acetate and the organic phase was dried over anhydrous magnesium sulfate. After the solvent was distilled off under reduced pressure, the resulting residue was purified by silica gel column chromatography (hexane:ethyl acetate=80:20–65:35) to give methyl 3-formyl-4-hydroxy-benzoate (7.24 g, 31%, mp 87.5–89.0° C.) as a colorless powder.

To a mixture of methyl 3-formyl-4-hydroxybenzoate (4.0 g, 22.2 mmol) and tetrahydrofuran (100 mL), 4-ethylphenyllithium [which had been prepared by stirring t-butyllithium (66 mmol) into a mixture of 1-bromo-4-ethylbenzene (12.3 g, 66 mmol) and tetrahydrofuran (200 mL) at −70° C. for 30 minutes] was added at −70° C. and stirred for 1 hour. After addition of saturated aqueous ammonium chloride, the reaction mixture was extracted with ethyl acetate, and the organic phase was washed with saturated aqueous sodium chloride and then dried over anhydrous magnesium sulfate. After the solvent was distilled off under reduced pressure, the resulting residue was purified by silica gel column chromatography (hexane:ethyl acetate=65:35–50:50) to give methyl 3-[(4-ethylphenyl)hydroxymethyl]benzoate (2.92 g, 46%) as a light-yellow gum.

The thus obtained methyl 3-[(4-ethylphenyl)hydroxymethyl]benzoate (2.88 g, 10.0 mmol), 10% palladium carbon (200 mg), concentrated hydrochloric acid (0.5 mL) and methanol (15 mL) were mixed and stirred under a hydrogen atmosphere at room temperature for 14 hours. After filtration to remove the insoluble materials, the solvent was distilled off under reduced pressure and the resulting residue was purified by silica gel column chromatography (hexane:ethyl acetate=80:20) to give methyl 3-(4-ethylbenzyl)-4-hydroxybenzoate (2.38 g, 88%) as a colorless powder.
mp 134.0–137.0° C.

Preparation Example 3

Preparation of 2-(4-ethylbenzyl)resorcinol

To a mixture of 1,3-dimethoxybenzene (6.9 g, 50 mmol) and tetrahydrofuran (70 mL), n-butyllithium (1.57 M in hexane, 35 mL) was added in ice and stirred for 1.5 hours. Subsequently, 4-ethylbenzyl bromide (10 g, 50 mmol) was added in ice and stirred for an additional 3.5 hours. After addition of saturated aqueous ammonium chloride, the reaction mixture was extracted with ethyl acetate, and the organic phase was washed with saturated aqueous sodium chloride and then dried over anhydrous magnesium sulfate. After the solvent was distilled off under reduced pressure, the resulting residue was purified by silica gel column chromatography (hexane:ethyl acetate=95:5–85:15) to give 1,3-dimethoxy-2-(4-ethylbenzyl)benzene (6.37 g, 49%, mp 62.5–66.5° C.) as a light-yellow powder.

A mixture of 1,3-dimethoxy-2-(4-ethylbenzyl)benzene (6.0 g, 23.4 mmol) and pyridine hydrochloride (21.6 g, 187 mmol) was heated and stirred at 180° C. for 15 hours. After addition of water, the reaction mixture was extracted with ethyl acetate, and the organic phase was washed with diluted aqueous hydrochloric acid and saturated aqueous sodium chloride and then dried over anhydrous magnesium sulfate. After the solvent was distilled off under reduced pressure, the resulting residue was purified by silica gel column chromatography (hexane:ethyl acetate=80:20) to give 2-(4-ethylbenzyl)resorcinol (5.2 g, 97%) as a light-brown oil.

Preparation Example 4

Preparation of 2-(4-trifluoromethylbenzyl)phenol

To a mixture of magnesium (3.44 g, 142 mmol) and tetrahydrofuran (10 mL), 4-bromobenzotrifluoride (2–3 mL) was added at room temperature. After confirming the initiation of the reaction, a solution of additional 4-bromobenzotrifluoride (total 20.9 g, 93.1 mmol) in tetrahydrofuran (56 mL) was added dropwise and stirred for 30 minutes under the same conditions. After the reaction mixture was cooled in ice, a solution of 2-benzyloxybenzaldehyde (16.4 g, 77.2 mmol) in tetrahydrofuran (20 mL) was added and stirred at room temperature for 1 hour. The reaction mixture was poured into saturated aqueous ammonium chloride and extracted with ethyl acetate. The organic phase was washed with saturated aqueous sodium chloride and then dried over anhydrous magnesium sulfate. After the solvent was distilled off under reduced pressure, the resulting residue was purified by neutral silica gel column chromatography (hexane:ethyl acetate=90:10–85:15) to give 2-benzyloxy-(4'-trifluoromethyl)diphenylmethanol.

The thus obtained 2-benzyloxy-(4'-trifluoromethyl)diphenylmethanol, 10% palladium/carbon (1.68 g), concentrated hydrochloric acid (3.4 mL) and methanol (330 mL) were mixed and stirred under a hydrogen atmosphere at room temperature for 14.5 hours. After filtration to remove the insoluble materials, the solvent was distilled off under reduced pressure and the resulting residue was purified by silica gel column chromatography (hexane:ethyl acetate=93:7–85:15) to give 2-(4-trifluoromethylbenzyl)phenol (17.5 g, 90%) as a colorless oil.

Preparation Example 5

Preparation of 2-(4-ethylbenzyl)-4-fluorophenol

To a mixture of 2-bromo-4-fluorophenol (24.7 g, 129 mmol), tetrabutylammonium iodide (4.8 g, 13.0 mmol), potassium carbonate (35.9 g, 260 mmol) and N,N-dimethylformamide (390 mL), benzyl bromide (23.5 g, 137 mmol) was added at room temperature and stirred for 1.5 hours. The reaction mixture was poured into a mixture of ethyl acetate and saturated aqueous sodium chloride, and then extracted with ethyl acetate. The organic phase was washed twice with saturated aqueous sodium chloride and then dried over anhydrous magnesium sulfate. After the solvent was distilled off under reduced pressure, the resulting residue was purified by silica gel column chromatography (hexane:ethyl acetate=90:10–80:20) to give 1-benzyloxy-2-bromo-4-fluorobenzene (33.0 g, 90%).

To a mixture of magnesium (3.2 g, 133 mmol) and tetrahydrofuran (10 mL), 1-benzyloxy-2-bromo-4-fluorobenzene (2–3 mL) was added at room temperature. After heating to start the reaction, a solution of additional 1-benzyloxy-2-bromo-4-fluorobenzene (total 30.0 g, 106 mmol) in tetrahydrofuran (60 mL) was added dropwise and stirred for 30 minutes under the same conditions. After the reaction mixture was cooled in ice, a solution of 4-ethylbenzaldehyde (16.4 g, 77.2 mmol) in tetrahydrofuran (20 mL) was added and stirred at room temperature for 3 hours. The reaction mixture was poured into saturated aqueous ammonium chloride and extracted with ethyl acetate. The organic phase was washed with saturated aqueous sodium chloride and then dried over anhydrous magnesium sulfate. After the solvent was distilled off under reduced pressure, the resulting residue was purified by neutral silica gel column chromatography (hexane:ethyl acetate=90:10–80:20) to give 2-benzyloxy-5-fluoro-(4'-ethyl)diphenylmethanol.

The thus obtained 2-benzyloxy-5-fluoro-(4'-ethyl)diphenylmethanol, 10% palladium carbon (1.77 g), concentrated hydrochloric acid (3.5 mL) and methanol (350 mL) were mixed and stirred under a hydrogen atmosphere at room temperature for 13 hours. After filtration to remove the insoluble materials, the solvent was distilled off under reduced pressure and the resulting residue was purified by silica gel column chromatography (hexane:ethyl acetate=90:10–80:20) to give 2-(4-ethylbenzyl)-4-fluorophenol (21.0 g, 85%) as a yellow oil.

Preparation Example 6

Preparation of 2-(4-acetylbenzyl)phenol

A mixture of 2-(4-methoxycarbonylbenzyl)phenol (250 mg, 1.03 mmol), methanol (1.0 mL) and 2M NaOH (4.0 mL) was stirred at 75° C. for 1 hour. After cooling on ice, the reaction mixture was adjusted to pH 3.0 with 1M hydrochloric acid. The resulting precipitates were extracted with ethyl acetate, and the organic phase was washed with saturated aqueous sodium chloride and then dried over anhydrous magnesium sulfate. After the solvent was distilled off under reduced pressure, the resulting residue (230 mg) was diluted with tetrahydrofuran (10 mL), followed by addition of N, O-dimethylhydroxyamine-hydrochloride (301 mg), triethylamine (0.456 mL), water (0.5 mL), WSC HCl (296 mg) and HOBT (210 mg). After stirring at room temperature for 2 hours, saturated aqueous NaHCO$_3$ was added to the reaction mixture. The mixture was extracted twice with ethyl acetate, and the combined organic phases were washed with saturated aqueous sodium chloride and dried over anhydrous magnesium sulfate.

After the solvent was concentrated, the resulting residue was purified by silica gel column chromatography (hexane:ethyl acetate=1:2) to give 4-(2-hydroxybenzyl)-N-methoxy-N-methylbenzamide (250 mg, 89%) as a colorless oil.

Next, 4-(2-hydroxybenzyl)-N-methoxy-N-methylbenzamide (250 mg, 0.921 mmol) was dissolved in tetrahydrofuran (10 mL), followed by addition of methylmagnesium bromide (12% in THF, 2.8 mL) at −20° C. After 15 minutes, a second addition of methylmagnesium bromide (12% in THF, 2.5 mL) was made, followed by a third addition of methylmagnesium bromide (12% in THF, 2.0 mL). After 10 minutes, saturated aqueous ammonium chloride was added to the reaction mixture, which was then extracted twice with ethyl acetate. The combined organic phases were washed with saturated aqueous sodium chloride and dried over anhydrous magnesium sulfate. After the solvent was concentrated, the resulting residue was purified by silica gel column chromatography (hexane:ethyl acetate=3:1) to give the titled compound (110 mg, 53%) as a colorless powder.

ESI m/z=249 (M+Na)

Preparation Example 7

Preparation of 2,3,4,6-tetra-O-acetyl-5-thio-D-glucopyranose

To a solution of 1,2,3,4,6-penta-O-acetyl-5-thio-D-glucopyranose (34.0 g, 0.0837 mol) in N,N-dimethylformamide (300 mL), a mixture of methylhydrazine (6.70 mL, 0.120 mmol), acetic acid (15 mL, 0.120 mmol) and N,N-dimethylformamide (10 mL) was added in ice. After stirring at room temperature for 2.5 hours, 0.5M HCl (300 mL) was added to the reaction mixture in ice, which was then extracted twice with ethyl acetate (250 mL). The combined organic phases were washed sequentially with water (200 mL), saturated aqueous NaHCO$_3$ (100 mL), water (100 mL) and saturated aqueous sodium chloride (100 mL), followed by addition of MgSO$_4$ and activated charcoal (1 g). After filtration to remove the insoluble materials, the filtrate was concentrated under reduced pressure. The resulting residue was crystallized from isopropyl ether (70 mL) to give 2,3,4,6-tetra-O-acetyl-5-thio-gluco-pyranose (26.9 g, 88%) as a colorless crystal.

EXAMPLES

The preparation method of the present invention will be further described in more detail in the following examples, which are not intended to limit the scope of the invention. Among the following examples, there are some cases where the yield is affected by the purity of starting materials, etc. When optimized preparation conditions are selected for each compound, it is possible to achieve a higher yield.

Example 1

Preparation of 2'-(4'-ethylbenzyl)phenyl 2,3,4,6-tetra-O-acetyl-5-thio-β-D-glucopyranoside 2,3,4,6-Tetra-O-acetyl-5-thio-D-glucopyranose (100 mg, 0.274 mmol), 2-(4-ethylbenzyl)phenol (117 mg, 0.551 mmol), triphenylphosphine (144 mg, 0.548 mmol) and THF (3 mL) were mixed, and to the resulting mixture, diethyl azodicarboxylate (40% in toluene, 0.24 mL) was then slowly added dropwise at room temperature. After stirring at room temperature for 20 hours, the reaction mixture was concentrated and the resulting residue was purified by silica gel column chromatography (hexane:ethyl acetate=7:3) to give the titled compound (12 mg, 11%) as a colorless powder.

$^1$H-NMR (300 MHz, CDCl$_3$): δ 1.20 (t, J=7.6 Hz, 3H), 1.90 (s, 3H), 2.01 (s, 3H), 2.04 (s, 3H), 2.05 (s, 3H), 2.60 (q, J=7.6 Hz, 2H), 3.20–3.30 (m, 1H), 3.88 (s, 2H), 4.08–4.17 (m, 1H), 4.25–4.35 (m, 1H), 5.16 (dd, J=8.9, 9.3 Hz, 1H), 5.33 (d, J=8.6 Hz, 1H), 5.39 (dd, J=9.3, 10.4 Hz, 1H), 5.62 (dd, J=8.6, 8.9 Hz, 1H), 6.94–7.00 (m, 1H), 7.04–7.14 (m, 6H), 7.17–7.24 (m, 1H).

ESI m/z=557 (M−H)

mp 114.0–119.0° C.

Example 2

Preparation of 4',6'-dibromo-2'-(4'-ethylbenzyl)phenyl 2,3,4,6-tetra-O-acetyl-5-thio-β-D-glucopyranoside 2,3,4,6-Tetra-O-acetyl-5-thio-D-glucopyranose (510 mg, 1.4 mmol), 4,6-dibromo-2-(4-ethylbenzyl)phenol (1.05 g, 2.8 mmol), triphenylphosphine (550 mg, 2.1 mmol) and toluene (8 mL) were mixed, and to the resulting mixture, diisopropyl azodicarboxylate (40% in toluene, 1.06 g, 2.1 mmol) was then slowly added dropwise in ice. After stirring at room temperature for 12 hours, the reaction mixture was concentrated and the resulting residue was purified by silica gel column chromatography (hexane:ethyl acetate=7:3) to give the titled compound (550 mg, 55%) as a colorless powder.

$^1$H-NMR (200 MHz, CDCl$_3$): δ 1.23 (t, J=7.5 Hz, 3H), 2.02 (s, 3H), 2.03 (s, 3H), 2.05 (s, 3H), 2.06 (s, 3H), 2.63 (q, J=7.5 Hz, 2H), 2.95 (m, 1H), (m, 1H), 3.92 (d, J=15.6 Hz, 1H), 4.02 (dd, J=3.3, 12.1 Hz, 1H), 4.12 (d, J=15.6 Hz, 1H), 4.31 (dd, J=5.1, 12.1 Hz, 1H), 5.11 (t, J=9.2 Hz, 1H), 5.34 (dd, J=9.2, 10.7 Hz, 1H), 5.52 (d, J=−9.2 Hz, 1H), 5.71 (t, J=9.2 Hz, 1H), 7.07–7.17 (m, 5H), 7.56 (d, J=2.4 Hz, 1H).

ESI m/z=737, 739, 740, 742 (M+Na).

mp 152.0–155.0° C.

Example 3

Preparation of 2'-(4'-ethylbenzyl)phenyl 5-thio-β-D-glucopyranoside

4',6'-Dibromo-2'-(4'-ethylbenzyl)phenyl 2,3,4,6-tetra-O-acetyl-5-thio-β-D-glucopyranoside (410 mg, 0.572 mmol), potassium carbonate (158 mg, 1.15 mmol), 10% palladium/activated charcoal (50% wet, 200 mg) and methanol (20 mL) were mixed and stirred under a hydrogen atmosphere at room temperature for 20 hours. The reaction mixture was filtered through celite to remove the insoluble materials and the filtrate was concentrated. The resulting residue was recrystallized from methanol/water to give the titled compound (177 mg, 79%) as a colorless powder.

$^1$H-NMR (300 MHz, MeOH-d$_4$): δ 1.19 (t, J=7.3 Hz, 3H), 2.58 (q, J=7.3 Hz, 2H), 2.88–2.95 (m, 1H), 3.29–3.31 (m, 1H), 3.55–3.60 (m, 1H), 3.74–3.83 (m, 2H), 3.90–3.93 (m, 1H), 3.97–3.99 (m, 2H), 5.17 (d, J=8.5 Hz, 1H), 6.91 (dt, J=1.2, 7.4 Hz, 1H), 7.10–7.19 (m, 6H), 7.27 (d, J=7.9 Hz, 1H)

ESI m/z=389 (M−H)

mp 156.5–157.5° C.

Example 4

Preparation of 4'-bromo-2'-benzoylphenyl 2,3,4,6-tetra-O-acetyl-5-thio-β-D-glucopyranoside 2,3,4,6-Tetra-O-acetyl-5-thio-D-glucopyranose (200 mg, 0.549 mmol), 4-bromo-2-benzoylphenol (773 mg, 2.79 mmol), triphenylphosphine (191 mg, 1.10 mmol) and toluene (1.6 mL) were mixed, and to the resulting mixture, diethyl azodicarboxylate (40% in toluene, 0.48 mL, 1.10 mmol) was then slowly added dropwise in ice. After stirring at room temperature for 12 hours, the reaction mixture was concentrated and the resulting residue was purified by silica gel column chromatography (hexane:ethyl acetate=7:3) to give the titled compound (282 mg).

$^1$H-NMR (300 MHz, CDCl$_3$): δ 1.89 (s, 3H), 1.94 (s, 3H), 2.01 (s, 3H), 2.06 (s, 3H), 3.23 (m, 1H), 4.08–4.14 (m, 2H), 5.16–5.25 (m, 3H), 7.19 (d, J=8.9 Hz, 1H), 7.43–7.48 (m, 3H), 7.57–7.61 (m, 2H), 7.74–7.77 (m, 2H).

ESI m/z=645, 647 (M+Na).

Example 5

Preparation of 4'-chloro-2'-benzylphenyl 2,3,4,6-tetra-O-acetyl-5-thio-β-D-glucopyranoside 2,3,4,6-Tetra-O-acetyl-5-thio-D-glucopyranose (200 mg, 0.549 mmol), 4-chloro-2-benzylphenol (601 mg, 2.75 mmol), triphenylphosphine (191 mg, 1.10 mmol) and toluene (1.6 mL) were mixed, and to the resulting mixture, diethyl azodicarboxylate (40% in toluene, 0.48 mL, 1.10 mmol) was then slowly added dropwise in ice. After stirring at room temperature for 12 hours, the reaction mixture was concentrated and the resulting residue was purified by silica gel column chromatography (hexane:ethyl acetate=7:3) to give the titled compound (173 mg, 56%).

$^1$H-NMR (300 MHz, CDCl$_3$): δ 1.91 (s, 3H), 2.01 (s, 3H), 2.05 (s, 3H), 2.06 (s, 3H), 3.28 (m, 1H), 3.88 (s, 2H), 4.14 (dd, J=3.7, 12.0 Hz, 1H), 4.30 (dd, J=5.3, 12.0 Hz, 1H), 5.16 (dd, J=8.8, 9.5 Hz, 1H), 5.31 (d, J=8.6 Hz, 1H), 5.39 (dd, J=9.5, 10.3 Hz, 1H), 5.60 (dd, J=8.6, 8.8 Hz, 1H), 7.03–7.35 (m, 8H).

ESI m/z=587, 589 (M+Na).

mp 111.0–114.0° C.

Example 6

Preparation of 2'-(4'-ethylbenzyl)-4'-methoxycarbonylphenyl 2,3,4,6-tetra-O-acetyl-5-thio-β-D-glucopyranoside 2,3,4,6-Tetra-O-acetyl-5-thio-D-glucopyranose (1.0 g, 2.74 mmol), methyl 3-(4-ethylbenzyl)-4-hydroxybenzoate (2.23 g, 8.25 mmol), triphenylphosphine (1.44 g, 5.48 mmol) and toluene (5 mL) were mixed, and to the resulting mixture, diisopropyl azodicarboxylate (40% in toluene, 2.77 g) was then slowly added dropwise in ice. After stirring at room temperature for 17 hours, the reaction mixture was concentrated and the resulting residue was purified by silica gel column chromatography (hexane:ethyl acetate=65:35–50:50) to give the titled compound (646 mg, 38%) as a colorless amorphous substance.

$^1$H-NMR (300 MHz, CDCl$_3$): δ 1.20 (t, J=7.6 Hz, 3H), 1.88 (s, 3H), 2.01 (s, 3H), 2.04 (s, 3H), 2.05 (s, 3H), 2.59 (q, J=7.6 Hz, 2H), 3.27–3.35 (m, 1H), 3.86 (s, 3H), 3.89 (s, 2H), 4.13 (dd, J=3.9 and 12.0 Hz, 1H), 4.30 (dd, J=5.4 and 12.0 Hz, 1H), 5.17 (dd, J=8.8 and 9.3 Hz, 1H), 5.40 (dd, J=9.3 and 10.3 Hz, 1H), 5.40 (d, J=8.5 Hz, 1H), 5.61 (dd, J=8.5 and 8.8 Hz, 1H), 7.03–7.11 (m, 4H), 7.13 (d, J=8.7 Hz, 1H), 7.83 (d, J=2.2 Hz, 1H), 7.92 (d, J=2.2 and 8.7 Hz, 1H).

ESI m/z=639 (M+Na)

Example 7

Preparation of 2'-acetyl-3'-hydroxy-5'-methylphenyl 2,3,4,6-tetra-O-acetyl-5-thio-β-D-glucopyranoside 2,3,4,6-Tetra-O-acetyl-5-thio-D-glucopyranose (200 mg, 0.55 mmol), 2-acetyl-5-methylresorcinol (182 mg, 1.10 mmol), triphenylphosphine (288 mg, 1.10 mmol) and toluene (2 mL) were mixed, and to the resulting mixture, diisopropyl azodicarboxylate (40% in toluene, 555 mg) was then slowly added dropwise in ice. After stirring at room temperature for 18 hours, the reaction mixture was concentrated and the resulting residue was purified by silica gel column chromatography (hexane:ethyl acetate=70:30–50:50) to give the titled compound (82 mg, 28%) as a light-yellow powder.

$^1$H-NMR (300 MHz, CDCl$_3$): δ 2.00 (s, 3H), 2.03 (s, 3H), 2.05 (s, 3H), 2.07 (s, 3H), 2.34 (s, 3H), 2.61 (s, 3H), 3.30–3.38 (m, 1H), 3.86 (s, 3H), 4.15 (dd, J=3.4 and 12.0 Hz, 1H), 4.35 (dd, J=5.0 and 12.0 Hz, 1H), 5.20 (dd, J=9.1 and 9.4 Hz, 1H), 5.39 (dd, J=9.4 and 9.6 Hz, 1H), 5.52 (d, J=8.9 Hz, 1H), 5.63 (dd, J=8.9 and 9.1 Hz, 1H), 6.42 (s, 1H), 6.50 (s, 1H), 13.14 (s, 1H).

ESI m/z=535 (M+Na).

mp 162.5–164.5° C.

Example 8

Preparation of 3'-acetoxy-2'-(4'-ethylbenzyl)phenyl 2,3,4,6-tetra-O-acetyl-5-thio-β-D-glucopyranoside 2,3,4,6-Tetra-O-acetyl-5-thio-D-glucopyranose (1.29 g, 3.54 mmol), 2-(4-ethylbenzyl)resorcinol (2.42 g, 10.6 mmol), triphenylphosphine (1.86 g, 7.09 mmol) and toluene (13 mL) were mixed, and to the resulting mixture, diisopropyl azodicarboxylate (40% in toluene, 3.58 g) was then slowly added dropwise in ice. After stirring at room temperature for 24 hours, the reaction mixture was concentrated and the resulting residue was purified by silica gel column chromatography (hexane:ethyl acetate=65:35–50:50) to give a crude product of 3-hydroxy-2-(4-ethylbenzyl)phenyl 2,3,4,6-tetra-O-acetyl-5-thio-β-D-glucopyranoside (338 mg). To a mixture of this crude product (338 mg) and pyridine (2 mL), acetic anhydride (0.5 mL) was added at room temperature. After stirring at room temperature for 20 hours, water was added to the reaction mixture, which was then extracted with ethyl acetate. The organic phase was washed with saturated aqueous sodium chloride and then dried over anhydrous magnesium sulfate. After the solvent was distilled off under reduced pressure, the resulting residue was purified by silica gel column chromatography (hexane:ethyl acetate=2:1) to give the titled compound (134 mg, 6%) as a light-yellow gum.

$^1$H-NMR (300 MHz, CDCl$_3$): δ 1.18 (t, J=7.6 Hz, 3H), 1.83 (s, 3H), 1.99 (s, 3H), 2.04 (s, 3H), 2.06 (s, 3H), 2.16 (s, 3H), 2.57 (q, J=7.6 Hz, 2H), 3.24–3.30 (m, 1H), 3.75–3.90 (m, 2H), 4.10 (dd, J=3.8 and 12.0 Hz, 1H), 4.29 (dd, J=5.2 and 12.0 Hz, 1H), 5.14 (dd, J=8.8 and 9.3 Hz, 1H), 5.32 (d, J=8.7 Hz, 1H), 5.36 (dd, J=9.5 and 10.0 Hz, 1H), 5.58 (dd, J=8.7 and 9.1 Hz, 1H), 6.82 (d, J=8.2 Hz, 1H), 6.98–7.07 (m, 5H), 7.20–7.30 (m, 1H).

ESI m/z=639 (M+Na)

Example 9

Preparation of 2'-(4'-methoxybenzyl)phenyl 2,3,4,6-tetra-O-acetyl-5-thio-β-D-glucopyranoside 2,3,4,6-Tetra-O-acetyl-5-thio-D-glucopyranose (2.00 g, 5.48 mmol), 2-(4-methoxybenzyl)phenol (5.88 g, 27.4 mmol), triphenylphosphine (2.88 g, 10.9 mmol) and THF (20 mL) were mixed, and to the resulting mixture, diethyl azodicarboxylate (40% in toluene, 4.79 g, 10.9 mmol) was then slowly added dropwise in ice. After stirring at room temperature for 20 hours, the reaction mixture was concentrated and the resulting residue was purified by silica gel column chromatography (hexane:ethyl acetate=65:35). The resulting crude product was recrystallized from methanol to give the titled compound (457 mg, 15%) as a colorless powder.

$^1$H-NMR (300 MHz, CDCl$_3$): δ 1.93 (s, 3H), 2.02 (s, 3H), 2.04 (s, 3H), 2.06 (s, 3H), 3.23–3.28 (m, 1H), 3.77 (s, 3H), 3.85 (s, 2H), 4.09–4.14 (m, 1H), 4.28–4.33 (m, 1H), 5.16 (dd, J=9.1, 9.3 Hz, 1H), 5.33 (d, J=8.7 Hz, 1H), 5.39 (dd, J=9.6, 10.2 Hz, 1H), 5.62 (dd, J=8.7, 9.0 Hz, 1H), 6.79–6.82 (m, 2H), 6.95–7.21 (m, 6H).

ESI m/z=583 (M+Na).

mp 87.0–89.0° C.

Example 10

Preparation of 2'-(4'-trifluoromethylbenzyl)phenyl 2,3,4,6-tetra-O-acetyl-5-thio-β-D-glucopyranoside 2,3,4,6-Tetra-O-acetyl-5-thio-D-glucopyranose (2.00 g, 5.48 mmol), 2-(4-trifluoromethylbenzyl)phenol (6.91 g, 27.4 mmol), triphenylphosphine (2.88 g, 10.9 mmol) and THF (20 mL) were mixed, and to the resulting mixture, diethyl azodicarboxylate (40% in toluene, 4.79 g, 10.9 mmol) was then slowly added dropwise in ice. After stirring at room temperature for 20 hours, the reaction mixture was concentrated and the resulting residue was purified by silica gel column chromatography (hexane:ethyl acetate=65:35). The resulting crude product was recrystallized from methanol to give the titled compound (630 mg, 19%) as a colorless powder.

$^1$H-NMR (300 MHz, CDCl$_3$): δ 1.90 (s, 3H), 2.01 (s, 3H), 2.05 (s, 6H), 3.23–3.30 (m, 1H), 3.96 (s, 2H), 4.07–4.13 (m, 1H), 4.27–4.32 (m, 1H), 5.16 (dd, J=9.0, 9.5 Hz, 1H), 5.34–5.41 (m, 2H), 5.57 (dd, J=8.5, 9.1 Hz, 1H), 7.01–7.29 (m, 6H), 7.50–7.53 (m, 2H).

ESI m/z=621 (M+Na).

mp 144.0–145.0° C.

Example 11

Preparation of 2'-(4'-fluorobenzyl)phenyl 2,3,4,6-tetra-O-acetyl-5-thio-β-D-glucopyranoside 2,3,4,6-Tetra-O-acetyl-5-thio-D-glucopyranose (2.00 g, 5.48 mmol), 2-(4-fluorobenzyl)phenol (5.54 g, 27.4 mmol), triphenylphosphine (2.88 g, 10.9 mmol) and toluene (20 mL) were mixed, and to the resulting mixture, diethyl azodicarboxylate (40% in toluene, 4.79 g, 10.9 mmol) was then slowly added dropwise in ice. After stirring at room temperature for 20 hours, the reaction mixture was concentrated and the resulting residue was purified by silica gel column chromatography (hexane:ethyl acetate=90:10). The resulting crude product was recrystallized from methanol to give the titled compound (751 mg, 25%) as a colorless powder.

$^1$H-NMR (300 MHz, CDCl$_3$): δ 1.93 (s, 3H), 2.02 (s, 3H), 2.04 (s, 3H), 2.05 (s, 3H), 3.23–3.30 (m, 1H), 3.87 (s, 2H), 4.09–4.14 (m, 1H), 4.27–4.33 (m, 1H), 5.16 (dd, J=9.0, 9.4 Hz, 1H), 5.33–5.41 (m, 2H), 5.59 (dd, J=8.7, 9.0 Hz, 1H), 6.91–7.26 (m, 8H).

ESI m/z=571 (M+Na).

mp 99.0–103.0° C.

Example 12

Preparation of 2'-(4'-ethylbenzyl)phenyl 2,4,6-tri-O-pivaloyl-5-thio-β-D-glucopyranoside 2,4,6-Tri-O-pivaloyl-5-thio-D-glucopyranose (200 mg, 0.446 mmol), 2-(4-ethylbenzyl)phenol (473 mg, 2.23 mmol), triphenylphosphine (155 mg, 0.892 mmol) and THF (1.6 mL) were mixed, and to the resulting mixture, diethyl azodicarboxylate (40% in toluene, 0.39 mL) was then slowly added dropwise at room temperature. After stirring at room temperature for 10 hours, the reaction mixture was concentrated and the resulting residue was purified by silica gel column chromatography (hexane:ethyl acetate=9:1) to give the titled compound (91 mg, 32%).

$^1$H-NMR (300 MHz, CDCl$_3$): δ 1.16 (s, 9H), 1.19 (s, 9H), 1.23 (s, 9H), 2.60 (q, J=7.7 Hz, 2H), 3.25 (m, 1H), 3.62 (dd, J=8.6, 9.2 Hz, 1H), 3.83 (d, J=15 Hz, 1H), 3.93 (d, J=15 Hz, 1H), 4.22 (m 2H), 5.27 (dd, J=9.2, 10.6 Hz, 1H), 5.37 (d, J=8.6 Hz, 1H), 5.49 (t, J=8.6 Hz, 1H), 6.92–7.20 (m, 8H).

ESI m/z=665 (M+Na).

Example 13

Preparation of 2'-(4'-ethylbenzyl)phenyl 2,3,4,6-tetra-O-benzoyl-5-thio-β-D-glucopyranoside 2,3,4,6-Tetra-O-benzoyl-5-thio-D-glucopyranose (200 mg, 0.33 mmol), 2-(4-ethylbenzyl)phenol (347 mg, 1.63 mmol), triphenylphosphine (171 mg, 0.65 mmol) and toluene (2 mL) were mixed, and to the resulting mixture, diethyl azodicarboxylate (40% in toluene, 284 mg) was then slowly added dropwise at room temperature. After stirring at room temperature for 16.5 hours, the reaction mixture was concentrated and the resulting residue was purified by silica gel column chromatography (hexane:ethyl acetate=4:1) to give the titled compound (41 mg, 15%) as a colorless amorphous substance.

$^1$H-NMR (300 MHz, CDCl$_3$): δ 1.16 (t, J=7.6 Hz, 3H), 2.53 (q, J=7.6 Hz, 2H), 3.70–3.80 (m, 1H), 3.76 (d, J=15.5 Hz, 1H), 3.87 (d, J=15.5 Hz, 1H), 4.54 (dd, J=5.1 and 12.0 Hz, 1H), 4.65 (dd, J=4.5 and 12.0 Hz, 1H), 5.65 (d, J=8.4 Hz, 1H), 5.84 (dd, J=9.1 and 9.5 Hz, 1H), 6.03 (dd, J=9.5 and 10.0 Hz, 1H), 6.17 (dd, J=8.4 and 9.1 Hz, 1H), 6.85–7.60 (m, 20H), 7.70–8.05 (m, 8H).

ESI m/z=829 (M+Na).

Example 14

Preparation of 2'-(4'-methylbenzyl)phenyl 2,3,4,6-tetra-O-acetyl-5-thio-β-D-glucopyranoside The same procedure as shown in Example 1 was repeated to give the titled compound as a colorless powder.

Yield 14%

ESI m/z=567 (M+Na)

mp 109.0–113.0° C.

Example 15

Preparation of 2'-(4'-ethoxybenzyl)phenyl 2,3,4,6-tetra-O-acetyl-5-thio-β-D-glucopyranoside 2,3,4,6-Tetra-O-acetyl-5-thio-D-glucopyranose (2.0 g, 5.48 mmol), 2-(4-ethoxybenzyl)phenol (6.25 g, 27.4 mmol), triphenylphosphine (2.88 g, 10.9 mmol) and tetrahydrofuran (20 mL) were mixed, and to the resulting mixture, diethyl azodicarboxylate (40% in toluene, 4.79 g) was then slowly added dropwise in ice. After stirring at room temperature for 17 hours, the reaction mixture was concentrated and the resulting residue was purified by silica gel column chromatography (hexane:ethyl acetate=65:35). The resulting powder was recrystallized from methanol to give the titled compound (598 mg, 19%) as a colorless powder.

ESI m/z=597 (M+Na)

mp 93.0–94.5° C.

Example 16

Preparation of 2'-(4'-ethylbenzyl)-4'-methylphenyl 2,3,4,6-tetra-O-acetyl-5-thio-β-D-glucopyranoside The same procedure as shown in Example 1 was repeated to give the titled compound as a colorless powder.

Yield 18%

ESI m/z=595 (M+Na)

mp 77.0–79.5° C.

Example 17

Preparation of 2'-(4'-ethylbenzyl)-4'-fluorophenyl 2,3,4,6-tetra-O-acetyl-5-thio-β-D-glucopyranoside The same procedure as shown in Example 1 was repeated to give the titled compound in a yield of 23% as a yellow amorphous substance.

$^1$H-NMR (300 MHz, CDCl$_3$): δ 1.22 (t, J=7.6 Hz, 3H), 1.94 (s, 3H), 2.02 (s, 3H), 2.04 (s, 3H), 2.06 (s, 3H), 2.61 (q, J=7.6 Hz, 2H), 3.21–3.28 (m, 1H), 3.86 (s, 2H), 4.10–4.15 (m, 1H), 4.31–4.34 (m, 1H), 5.15 (dd, J=9.0 and 9.5 Hz, 1H), 5.25 (d, J=8.7 Hz, 1H), 5.39 (dd, J=9.6 and 10.3 Hz, 1H), 5.61 (dd, J=8.7 and 9.0 Hz, 1H), 6.71–7.13 (m, 7H)

ESI m/z=599 (M+Na)

Example 18

Preparation of 4'-bromo-2'-(4'-ethylbenzyl)phenyl 2,3,4,6-tetra-O-acetyl-5-thio-β-D-glucopyranoside The same procedure as shown in Example 1 was repeated to give the titled compound in a yield of 36% as a yellow amorphous substance.

$^1$H-NMR (300 MHz, CDCl$_3$): δ 1.21 (t, J=7.6 Hz, 3H), 1.91 (s, 3H), 2.01 (s, 3H), 2.04 (s, 3H), 2.06 (s, 3H), 2.61 (q, J=7.6 Hz, 2H), 3.25–3.30 (m, 1H), 3.84 (s, 2H), 4.10–4.15 (m, 1H), 4.27–4.33 (m, 1H), 5.15 (dd, J=8.5 and 8.7 Hz, 1H), 5.38 (t, J=8.9 Hz, 1H), 5.60 (dd, J=8.7 and 8.9 Hz, 1H), 6.98–7.32 (m, 7H).

ESI m/z=659 (M+Na).

Example 19

Preparation of 2'-benzylphenyl 2,3,4,6-tetra-O-acetyl-5-thio-β-D-glucopyranoside The same procedure as shown in Example 1 was repeated to give the titled compound in a yield of 18% as a colorless powder.

ESI m/z=553 (M+Na).

mp 124.5–125.5° C.

Example 20

Preparation of 2'-(4'-benzoyloxybenzyl)phenyl 2,3,4,6-tetra-O-acetyl-5-thio-β-D-glucopyranoside The same procedure as shown in Example 1 was repeated to give the titled compound in a yield of 16% as a colorless amorphous substance.

$^1$H-NMR (300 MHz, CDCl$_3$): δ 1.94 (s, 3H), 2.03 (s, 3H), 2.06 (s, 3H), 2.08 (s, 3H), 3.26–3.30 (m, 1H), 3.94 (s, 2H), 4.10–4.16 (m, 1H), 4.29–4.34 (m, 1H), 5.18 (dd, J=8.7 and 9.0 Hz, 1H), 5.34–5.40 (m, 2H), 5.62 (dd, J=8.5 and 9.0 Hz, 1H), 7.00–7.27 (m, 8H), 7.47–7.63 (m, 3H), 8.17–8.20 (m, 2H).

ESI m/z=673 (M+Na).

Example 21

Preparation of 2'-[4'-(2'-benzoyloxyethyl)benzyl]phenyl 2,3,4,6-tetra-O-acetyl-5-thio-β-D-glucopyranoside The same procedure as shown in Example 1 was repeated to give the titled compound as a yellow oil.

$^1$H-NMR (300 MHz, CDCl$_3$): δ 1.90 (s, 3H), 2.01 (s, 3H), 2.05 (s, 3H), 2.08 (s, 3H), 3.04 (t, J=7.0 Hz, 2H), 3.28–3.30 (m, 1H), 3.90 (s, 2H), 4.10–4.17 (m, 1H), 4.28–4.47 (m, 1H), 4.50 (t, J=7.0 Hz, 2H), 5.13–5.19 (m, 1H), 5.32–5.39 (m, 2H), 5.62 (dd, J=8.7 and 8.9 Hz, 1H), 6.97–7.27 (m, 8H), 7.40–7.55 (m, 3H), 7.99–8.03 (m, 2H).

ESI m/z=701 (M+Na).

Example 22

Preparation of 2'-(4'-ethylbenzyl)-5'-(methoxymethyloxy)phenyl 2,3,4,6-tetra-O-acetyl-5-thio-β-D-glucopyranoside The same procedure as shown in Example 1 was repeated to give the titled compound in a yield of 23% as a colorless gum.

$^1$H-NMR (300 MHz, CDCl$_3$): δ 1.20 (t, J=7.6 Hz, 3H), 1.90 (s, 3H), 2.00 (s, 3H), 2.04 (s, 3H), 2.06 (s, 3H), 2.59 (q, J=7.6 Hz, 2H), 3.21–3.31 (m, 1H), 3.48 (s, 3H), 3.81 (s, 2H), 4.13 (dd, J=3.7 and 11.8 Hz, 1H), 4.31 (dd, J=5.1 and 11.8 Hz, 1H), 5.12–5.20 (m, 1H), 5.15 (s, 2H), 5.28 (d, J=8.7 Hz, 1H), 5.38 (dd, J=9.5 and 10.3 Hz, 1H), 5.60 (dd, J=8.7 and 9.0 Hz, 1H), 6.68 (dd, J=2.3 and 8.4 Hz, 1H), 6.83 (d, J=2.3 Hz, 1H), 6.96 (d, J=8.4 Hz, 1H), 7.02–7.11 (m, 4H).

ESI m/z=641 (M+Na).

Example 23

Preparation of 2'-(4'-ethylbenzyl)-4'-chlorophenyl 2,3,4,6-tetra-O-acetyl-5-thio-β-D-glucopyranoside The same procedure as shown in Example 1 was repeated to give the titled compound in a yield of 28% as a light-yellow gum.

$^1$H-NMR (300 MHz, CDCl$_3$): δ 1.21 (t, J=7.6 Hz, 3H), 1.92 (s, 3H), 2.01 (s, 3H), 2.04 (s, 3H), 2.06 (s, 3H), 2.61 (q, J=7.6 Hz, 2H), 3.23–3.30 (m, 1H), 3.84 (s, 2H), 4.13 (dd, J=3.7 and 8.1 Hz, 1H), 4.25–4.36 (m, 1H), 5.14 (dd, J=9.0 and 9.5 Hz, 1H), 5.28 (d, J=8.7 Hz, 1H), 5.37 (dd, J=9.5 and 10.2 Hz, 1H), 5.60 (dd, J=8.7 and 9.0 Hz, 1H), 7.00–7.20 (m, 7H).

ESI m/z=615 (M+Na)

Example 24

Preparation of 5'-acetyloxymethyl-2'-(4'-ethylbenzyl)phenyl 2,3,4,6-tetra-O-acetyl-5-thio-β-D-glucopyranoside 2,3,4,6-Tetra-O-acetyl-5-thio-D-glucopyranose (1.0 g, 2.7 mmol), 5-acetyloxymethyl-2-(4-ethylbenzyl)phenol (1.5 g, 5.3 mmol), triphenylphosphine (941 mg, 5.4 mmol) and toluene (5 mL) were mixed, and to the resulting mixture, diisopropyl azodicarboxylate (40% in toluene, 3.2 mL) was then added dropwise in ice. After stirring at room temperature for 22 hours, the reaction mixture was concentrated and the resulting residue was purified by silica gel column chromatography (hexane:ethyl acetate=6:4) to give the titled compound (670 mg, 39%) as a colorless amorphous substance.

$^1$H-NMR (200 MHz, CDCl$_3$): δ 1.20 (t, J=7.7 Hz, 3H), 1.99 (s, 3H), 2.01 (s, 3H), 2.05 (s, 3H), 2.06 (s, 3H), 2.11 (s, 3H), 2.60 (q, J=7.7 Hz, 2H), 3.29 (ddd, J=4.0, 5.2, 10.1 Hz, 1H), 3.86–3.92 (m, 2H), 4.13 (dd, J=4.0, 12.0 Hz, 1H), 4.31 (dd, J=5.2, 12.0 Hz, 1H), 5.05–5.07 (m, 2H), 5.17 (dd, J=8.8, 9.4 Hz, 1H), 5.33 (d, J=8.8 Hz, 1H), 5.40 (dd, J=9.4, 10.1 Hz, 1H), 5.61 (d, J=8.8 Hz, 1H), 6.95–7.15 (m, 7H).

ESI m/z=653 (M+Na).

Example 25

Preparation of 2'-nitrophenyl 2,3,4,6-tetra-O-acetyl-5-thio-β-D-glucopyranoside 2,3,4,6-Tetra-O-acetyl-5-thio-D-glucopyranose (500 mg, 1.37 mmol), 2-nitrophenol (382 mg, 2.74 mmol), triphenylphosphine (477 mg, 2.74 mmol) and toluene (2.5 mL) were mixed, and to the resulting mixture, diisopropyl azodicarboxylate (40% in toluene, 1.62 mL) was then slowly added dropwise in ice. After stirring at room temperature for 5.5 hours, the reaction mixture was concentrated and the resulting residue was purified by silica gel column chromatography (hexane:ethyl acetate=70:30) to give the titled compound (445 mg, 67%) as a light-yellow powder.

ESI m/z=508 (M+Na).

mp 170.0–171.5° C.

The same procedures as shown in the above examples were also repeated to synthesize the compounds summarized in the table below.

TABLE

| Example | Ar* | $R^1=R^2=R^3=R^4=$ | Yield in Mitsunobu reaction (%) | ESI Mas (M + Na) and mp (° C.) |
|---|---|---|---|---|
| 26 | 5-bromo-2-(4-methylbenzoyl)phenyl | Ac | 40 | 674 |
| 27 | 3,5-dibromo-2-(pyridin-4-ylmethyl)phenyl | Ac | 42 | 688<br>690<br>712<br>714 |
| 28 | 2-(benzyloxy)phenyl | Ac | 24 | 569 |
| 29 | biphenyl-2-yl | Ac | 47 | 539 |
| 30 | 5-chloro-2-(phenylcarbamoyl)phenyl | Ac | 38 | 616 |
| 31 | 2-(3-phenylpropanoyl)phenyl | Ac | 24 | 595 |

TABLE-continued
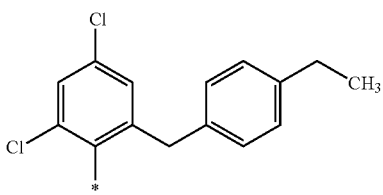
| Example | Ar* | R¹=R²=R³=R⁴= | Yield in Mitsunobu reaction (%) | ESI Mas (M + Na) and mp (° C.) |
|---|---|---|---|---|
| 32 | 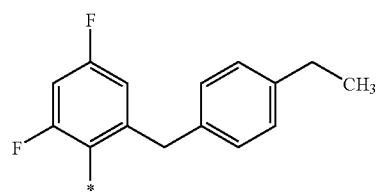 | Ac | 60 | 649<br>652 |
| 33 | 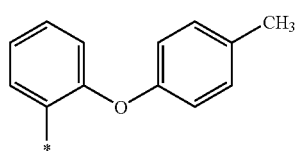 | Ac | 58 | 617 |
| 34 | 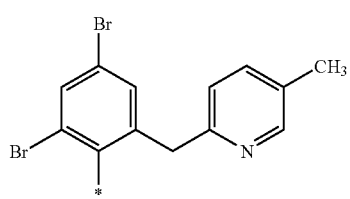 | Ac | 37 | 569 |
| 35 | 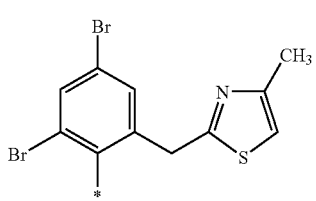 | Ac | 69 | 724<br>732<br>734 |
| 36 | 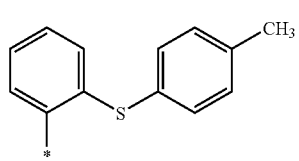 | Ac | 53 | 730<br>732<br>734 |
| 37 | 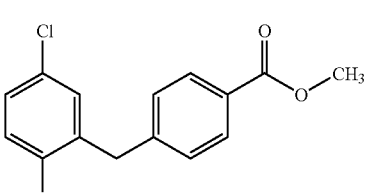 | H | 12[#] | 417<br>mp 140.0–142.0 |
| 38 |  | H | 20[#] | 443<br>mp 74.0–76.0 |

TABLE-continued
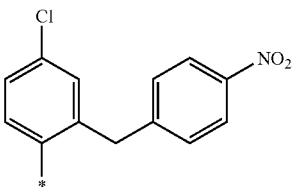
| Example | Ar* | $R^1=R^2=R^3=R^4=$ | Yield in Mitsunobu reaction (%) | ESI Mas (M + Na) and mp (° C.) |
|---|---|---|---|---|
| 39 | 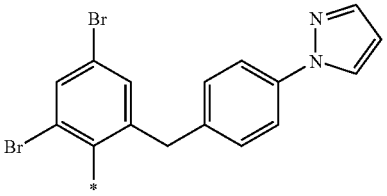 | Ac | 47 | 632<br>634 |
| 40 | 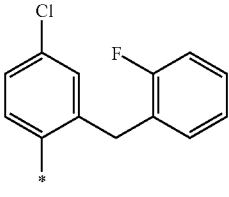 | Ac | 42 | 775<br>777<br>779 |
| 41 | 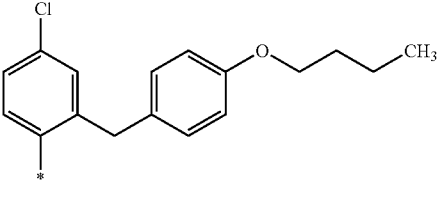 | H | 30[#] | 437<br>439<br>mp 170.0–173.0 |
| 42 | 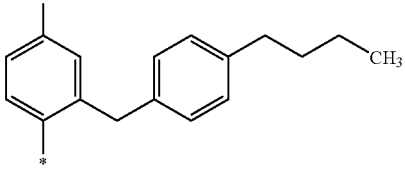 | H | 3.9[#] | 491<br>493<br>mp 166.0–169.0 |
| 43 | 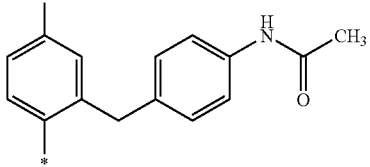 | H | 29[#] | 475<br>477<br>mp 165.0–168.0 |
| 44 |  | H | 20[#] | 476<br>478<br>mp 235.0–236.5 |

TABLE-continued

| Example | Ar* | R¹=R²=R³=R⁴= | Yield in Mitsunobu reaction (%) | ESI Mas (M + Na) and mp (° C.) |
|---|---|---|---|---|
| 45 | 2-(4-(ethylthio)benzyl)phenyl | H | 2.6# | 455<br>mp 174.0–176.5 |
| 46 | 3-(4-ethylbenzyl)phenyl | H | 30# | 413<br>mp 132.0–134.0 |
| 47 | 4-(4-ethylbenzyl)phenyl | H | 37# | 413<br>mp 137.0–138.0 |
| 48 | 4-chloro-2,6-bis(2-chloro-6-fluorobenzyl)phenyl | H | 33# | 613<br>615<br>617<br>619<br>mp 112.0–118.0 |
| 49 | 4-bromo-2-(1-ethyl-1H-pyrazole-4-carbonyl)phenyl | Ac | 44 | 663<br>665 |
| 50 | 4-bromo-2-(1-methyl-1H-pyrazole-4-carbonyl)phenyl | Ac | 38 | 649<br>651 |
| 51 | 2,4-dibromo-6-(3-ethylbenzyl)phenyl | Ac | 25 | 737<br>739<br>741 |

TABLE-continued

| Example | Ar* | R¹=R²=R³=R⁴= | Yield in Mitsunobu reaction (%) | ESI Mas (M + Na) and mp (° C.) |
|---|---|---|---|---|
| 52 | 2,4-dibromo-(2-ethylbenzyl)phenyl | Ac | 26 | 737<br>739<br>741 |
| 53 | 4-chloro-2-(2-fluoro-6-chlorobenzyl)phenyl | Ac | 10 | 639<br>641 |
| 54 | 4-chloro-2-(2,4-difluorobenzyl)phenyl | H | 31[#] | 455<br>457<br>mp 175.5–177.0 |
| 55 | 4-chloro-2-(3-fluorobenzyl)phenyl | Ac | 39 | 605<br>607 |
| 56 | 4-chloro-2-(3-phenoxybenzyl)phenyl | H | 5[#] | 511<br>513<br>mp 124.5–127.0 |
| 57 | 4-chloro-2-(4-isopropylbenzyl)phenyl | H | 5[#] | 461<br>463<br>mp 146.0–148.5 |

TABLE-continued

| Example | Ar* | $R^1=R^2=R^3=R^4=$ | Yield in Mitsunobu reaction (%) | ESI Mas (M + Na) and mp (° C.) |
|---|---|---|---|---|
| 58 | 4-F, 2-(4-ethylbenzyl)phenyl | H | 22# | 431<br>mp 156.0–157.0 |
| 59 | 3,5-dibromo-2-(2,4,6-trimethoxybenzyl)phenyl | Ac | 28 | 799<br>801<br>803 |
| 60 | 5-chloro-2-(2,3,5,6-tetrafluorobenzyl)phenyl | H | 41# | 491<br>493<br>mp 204.0–211.0 |
| 61 | 5-chloro-2-(biphenyl-4-ylmethyl)phenyl | H | 10# | 495<br>497<br>mp 187.0–195.0 |
| 62 | 5-chloro-2-(naphthalen-1-ylmethyl)phenyl | H | 5.2# | 469<br>471<br>mp 170.0–175.0 |
| 63 | 5-chloro-2-(3-trifluoromethoxybenzyl)phenyl | H | 28# | 503<br>505<br>mp 146.0–148.0 |

TABLE-continued

[Structure: cyclohexane ring with Ar-O, R¹O, R²O, R³O, R⁴OCH₂ substituents]

| Example | Ar* | R¹=R²=R³=R⁴= | Yield in Mitsunobu reaction (%) | ESI Mas (M + Na) and mp (° C.) |
|---|---|---|---|---|
| 64 | [5-chloro-2-(2,4-dichlorobenzyl)phenyl] | H | 38# | 487 / 489 / 481 / mp 172.0–174.0 |
| 65 | [5-chloro-2-(naphthalen-2-ylmethyl)phenyl] | H | 3.8# | 469 / 471 / mp 192.0–194.0 |
| 66 | [5-chloro-2-(4-pentyloxybenzyl)phenyl] | H | 5.0# | 505 / 507 / mp 143.0–144.5 |
| 67 | [3,5-dibromo-2-(4-morpholinophenylmethyl)phenyl] | Ac | 15 | 794 / 769 / 798 |
| 68 | [2-(4-piperidinophenylmethyl)phenyl] | H | 6.0# | 468 / mp 156.5–160.0 |
| 69 | [5-chloro-2-(4-tert-butylbenzyl)phenyl] | H | 27# | 475 / 477 / mp 79.0–82.5 |

TABLE-continued

| Example | Ar* | R¹=R²=R³=R⁴= | Yield in Mitsunobu reaction (%) | ESI Mas (M + Na) and mp (° C.) |
|---|---|---|---|---|
| 70 | 5-chloro-2-(3-trifluoromethyl-5-fluorobenzyl)phenyl | H | 31[#] | 505<br>507<br>mp 126.0–129.0 |
| 71 | 5-chloro-2-(2-(2-phenylethyl)benzyl)phenyl | H | 18[#] | 523<br>525<br>mp 128.0–130.0 |
| 72 | 5-chloro-2-(2-benzylbenzyl)phenyl | H | 22[#] | 509<br>511<br>150.5–151.5 |
| 73 | 5-chloro-2-(2,4-dimethoxybenzyl)phenyl | H | 7.5[#] | 479<br>481<br>mp 195.5–197.0 |
| 74 | 5-chloro-2-(2-ethoxybenzyl)phenyl | H | 15[#] | 463<br>465<br>mp 196.5–198.5 |

TABLE-continued

| Example | Ar* | R¹=R²=R³=R⁴= | Yield in Mitsunobu reaction (%) | ESI Mas (M + Na) and mp (° C.) |
|---|---|---|---|---|
| 75 | 5-chloro-2-(2-methylbenzyl)phenyl | H | 25# | 433<br>435<br>mp 147.0–149.0 |
| 76 | 2-[4-(4-ethylpiperazin-1-yl)benzyl]phenyl | H | 1# | 497 |
| 77 | 2-hydroxy-6-[N-(4-methoxybenzyl)carbamoyl]phenyl | Ac | 18 | 642 |
| 78 | 2-(4-carbamoylbenzyl)phenyl | H | 6# | 428<br>mp 215.5–216.0 |
| 79 | 2-[4-(N,N-dimethylcarbamoyl)benzyl]phenyl | H | 8# | 456<br>mp 193.5–194.0 |
| 80 | 2-(4-acetylbenzyl)phenyl | Ac | 18 | 595 |

TABLE-continued

|  | Ar |  |  |  |
|---|---|---|---|---|
| Example | Ar* | R¹=R²=R³=R⁴= | Yield in Mitsunobu reaction (%) | ESI Mas (M + Na) and mp (° C.) |
| 81 | (2-benzyl-4-cyclopropylphenyl) | H | 11# | 425<br>mp 148.0–148.5 |
| 82 | (3-(N-phenylcarbamoyl)naphth-2-yl) | H | 19# | 464<br>mp 200.0–202.0 |

Yield after deprotection of the acetyl groups

INDUSTRIAL APPLICABILITY

The present invention enables the provision of a method for selective chemical synthesis of aryl 1,2-trans-5-thioglycosidic linkages (β-5-thioglycosides). According to the method of the present invention, it is possible to provide a method for preparing an aryl 5-thio-β-D-aldohexopyranoside derivative useful as an SGLT2 inhibitor, or a synthetic intermediate thereof.

The invention claimed is:

1. A method for preparing an aryl 5-thio-β-D-aldohexopyranoside derivative of Formula (III), which comprises reacting a 5-thio-D-aldohexopyranose derivative of Formula (I) with Ar-OH of Formula (II) in the presence of a phosphine represented by $PR^{11}R^{12}R^{13}$ and an azo reagent represented by $R^{21}-N=N-R^{22}$ in accordance with the following scheme:

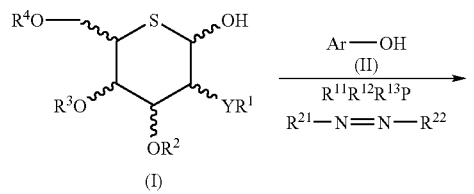

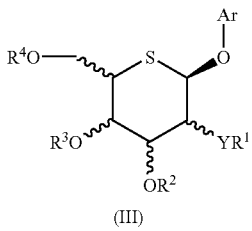

wherein
in the above Formulae (I) and (III),
the wavy lines mean containing any stereoisomer selected from D-form, L-form and a mixture thereof,
Y represents —O— or —NH—, and
$R^1$, $R^2$, $R^3$ and $R^4$, which may be the same or different, each represent a hydrogen atom, a $C_{2-10}$ acyl group, a $C_{1-6}$ alkyl group, a $C_{7-10}$ aralkyl group, a $C_{1-6}$ alkoxy-$C_{7-10}$ aralkyl group, an allyl group, a tri($C_{1-6}$ alkyl)silyl group, a $C_{1-6}$ alkoxy-$C_{1-6}$ alkyl group or a $C_{2-6}$ alkoxycarbonyl group, or
when Y represents —O—, $R^1$ and $R^2$, $R^2$ and $R^3$, or $R^3$ and $R^4$ may together form —C($R^A$)($R^B$)— wherein $R^A$ and $R^B$, which may be the same or different, each represent a hydrogen atom, a $C_{1-6}$ alkyl group or a phenyl group, in the above Formula (II),
Ar represents an aryl group which may be substituted with any substituent, in $PR^{11}R^{12}R^{13}$, $R^{11}$ to $R^{13}$, which may be the same or different, each represent a phenyl group which may be substituted with a $C_{1-6}$ alkyl group, a pyridyl group or a $C_{1-6}$ alkyl group, and in $R^{21}$—N=N—$R^{22}$, $R^{21}$ and $R^{22}$, which may be the same or different, each represent a $C_{2-5}$ alkoxycarbonyl group, an N,N-di-$C_{1-4}$ alkylaminocarbonyl group or a piperidinocarbonyl group.

2. The method according to claim 1, wherein

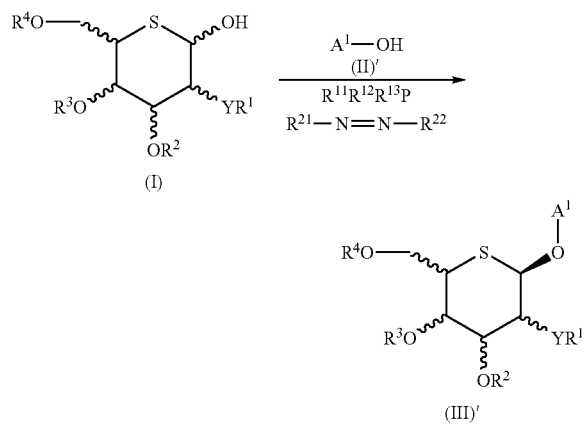

Formula (II) is represented by the above Formula (II)' and Formula (III) is represented by the above Formula (III)' wherein Y, $R^1$, $R^2$, $R^3$ and $R^4$ are as defined in claim 1, wherein in the above Formulae (II)' and (III)', $A^1$ represents an aryl group which may be substituted with the same or different 1 to 4 substituents selected from the group consisting of:

a halogen atom;

a hydroxyl group;

—$^+NH_3$;

—$^+N(CH_3)_3$;

a $C_{1-6}$ alkyl group which may be substituted with 1 to 4 substituents selected from the group consisting of a halogen atom and a hydroxyl group;

a group represented by the formula:

—(CH$_2$)m-Q wherein m represents an integer of 0 to 4, and Q represents a formyl group, an amino group, a nitro group, a cyano group, a carboxyl group, a sulfonic acid group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N-($C_{1-6}$ alkyl)aminocarbonyl group, or an N,N-di($C_{1-6}$ alkyl)aminocarbonyl group;

a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group; and a group represented by the formula:

—X-$A^2$ wherein X represents —(CH$_2$)n-, —CO(CH$_2$)n-, —CH(OH)(CH$_2$)n-, —O—(CH$_2$)n-, —CONH(CH$_2$)n-, —NHCO(CH$_2$)n- wherein n represents an integer of 0 to 3, —COCH=CH—, —S— or —NH—, and $A^2$ represents an aryl group, a heteroaryl group or a 4- to 6-membered heterocycloalkyl group, each of which may be substituted with the same or different 1 to 4 substituents selected from:

a halogen atom;

a hydroxyl group;

a $C_{1-6}$ alkyl group which may be substituted with 1 to 4 substituents selected from the group consisting of a halogen atom and a hydroxyl group;

a group represented by the formula:

—(CH$_2$)m'-Q' wherein m' represents an integer of 0 to 4, and Q' represents a formyl group, an amino group, a nitro group, a cyano group, a carboxyl group, a sulfonic acid group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N-($C_{1-6}$ alkyl)aminocarbonyl group, or an N,N-di($C_{1-6}$ alkyl)aminocarbonyl group; and a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group.

3. The method according to claim 2, wherein

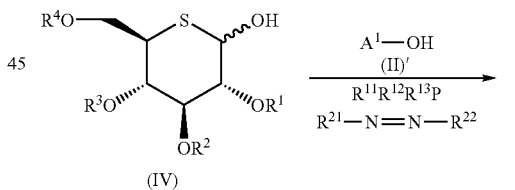

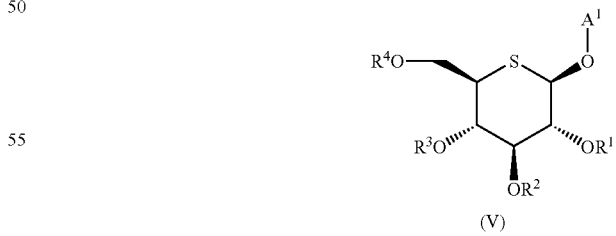

Formula (I) is represented by the above Formula (IV) wherein $R^1$, $R^2$, $R^3$ and $R^4$ are as defined in claim 1 and Formula (III)' is represented by the above Formula (V) wherein $R^1$, $R^2$, $R^3$ and $R^4$ are as defined in claim 1, and $A^1$ is as defined in claim 2.

4. The method according to claim 3, wherein $A^1$ represents a phenyl group substituted with —X-$A^2$ wherein X and $A^2$ are as defined in claim 2, in which the phenyl group may be further substituted with the same or different 1 to 3 substituents selected from:
- a halogen atom;
- a hydroxyl group;
- a $C_{1-6}$ alkyl group which may be substituted with 1 to 4 substituents selected from the group consisting of a halogen atom and a hydroxyl group;
- a group represented by the formula:

—(CH$_2$)m-Q wherein m and Q are as defined in claim 2; and
- a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group.

5. The method according to claim 3, wherein $A^1$ is represented by the following formula:

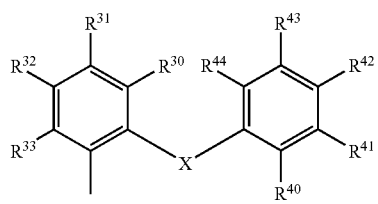

(VI)

wherein
X represents —(CH$_2$)n-, —CO(CH$_2$)n-, —CH(OH)(CH$_2$)n-, —O—(CH$_2$)n-, —CONH(CH$_2$)n-, —NHCO(CH$_2$)n- wherein n represents an integer of 0 to 3, —COCH=CH—, —S— or —NH—, $R^{30}$, $R^{31}$, $R^{32}$ and $R^{33}$, which may be the same or different, each represent:
- a hydrogen atom;
- a halogen atom;
- a hydroxyl group;
- —$^+$NH$_3$;
- —$^+$N(CH$_3$)$_3$;
- a $C_{1-6}$ alkyl group which may be substituted with 1 to 4 substituents selected from the group consisting of a halogen atom and a hydroxyl group;
- a group represented by the formula:

—(CH$_2$)m-Q wherein m represents an integer of 0 to 4, and Q represents a formyl group, an amino group, a nitro group, a cyano group, a carboxyl group, a sulfonic acid group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N-($C_{1-6}$ alkyl)aminocarbonyl group, or an N,N-di($C_{1-6}$ alkyl)aminocarbonyl group; or
- a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group, and $R^{40}$, $R^{41}$, $R^{42}$, $R^{43}$ and $R^{44}$, which may be the same or different, each represent:
- a hydrogen atom;
- a halogen atom;
- a hydroxyl group;
- a $C_{1-6}$ alkyl group which may be substituted with 1 to 4 substituents selected from the group consisting of a halogen atom and a hydroxyl group;
- a group represented by the formula:

—(CH$_2$)m'-Q' wherein m' represents an integer of 0 to 4, and Q' represents a formyl group, an amino group, a nitro group, a cyano group, a carboxyl group, a sulfonic acid group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylthio group, a $C_{1-6}$ alkylsulfinyl group, a $C_{1-6}$ alkylsulfonyl group, —NHC(=O)H, a $C_{2-10}$ acylamino group, a $C_{1-6}$ alkylsulfonylamino group, a $C_{1-6}$ alkylamino group, an N,N-di($C_{1-6}$ alkyl)amino group, a carbamoyl group, an N-($C_{1-6}$ alkyl)aminocarbonyl group, or an N,N-di($C_{1-6}$ alkyl)aminocarbonyl group; or
- a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, a $C_{7-10}$ aralkylamino group, a heteroaryl group, or a 4- to 6-membered heterocycloalkyl group, provided that each of these groups may be substituted with 1 to 4 substituents selected from the group consisting of a halogen atom, a hydroxyl group, a $C_{1-6}$ alkyl group and a $C_{1-6}$ alkoxy group.

6. The method according to claim 5, wherein $A^1$ is represented by the following formula:

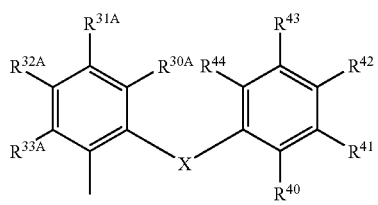

(VI)

wherein
X is as defined in claim 5,
$R^{30A}$, $R^{31A}$, $R^{32A}$ and $R^{33A}$, which may be the same or different, each represent:
- a hydrogen atom;
- a halogen atom;
- a hydroxyl group;
- a $C_{1-6}$ alkyl group which may be substituted with 1 to 4 substituents selected from the group consisting of a halogen atom and a hydroxyl group;
- a group represented by the formula:

—(CH$_2$)m$^4$-Q$^4$ wherein m$^4$ represents an integer of 0 to 4, and Q$^4$ represents a formyl group, a carboxyl group, a $C_{1-6}$ alkoxy group which may be substituted with 1 to 4 halogen atoms, a $C_{1-6}$ alkoxy-$C_{1-6}$ alkoxy group, a $C_{2-10}$ acyloxy group, a $C_{2-10}$ acyl group, a $C_{2-6}$ alkoxycarbonyl group, a $C_{1-6}$ alkylsulfonyl group, or a $C_{2-10}$ acylamino group; or a $C_{3-7}$ cycloalkyl group, a $C_{3-7}$ cycloalkyloxy group, an aryl group, a $C_{7-10}$ aralkyl group, an aryloxy group, a $C_{7-10}$ aralkyloxy group, or a $C_{7-10}$ aralkylamino group, provided that each of these groups may be substituted with 1 to 4 substituents selected from the group consisting of a halogen atom, a hydroxyl group, a $C_{1-6}$ alkyl group and a $C_{1-6}$ alkoxy group, and $R^{40}$, $R^{41}$, $R^{42}$, $R^{43}$ and $R^{44}$ are as defined in claim 5.

7. The method according to claim 3, wherein the compound of Formula (V) is a compound represented by the following formula:

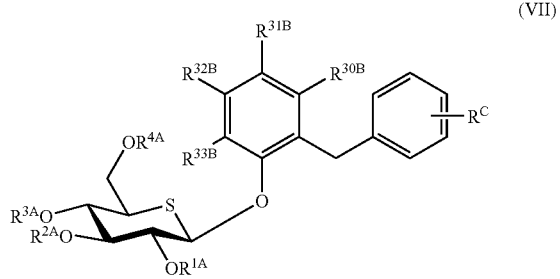

(VII)

wherein $R^{30B}$, $R^{31B}$, $R^{32B}$ and $R^{33B}$, which may be the same or different, each represent a hydrogen atom, a halogen atom, a $C_{1-6}$ alkyl group, a $C_{1-6}$ alkoxy group, a $C_{1-6}$ alkoxy-$C_{1-6}$ alkoxy group, a carboxyl group, a $C_{2-6}$ alkoxycarbonyl group, a hydroxyl group or a hydroxy-$C_{1-4}$ alkyl group, $R^C$ represents a hydrogen atom, a halogen atom, a $C_{1-6}$ alkyl group, a $C_{1-6}$ alkoxy group, a hydroxy-$C_{1-4}$ alkyl group, a halogen-substituted $C_{1-6}$ alkyl group or a $C_{1-6}$ alkylthio group, $R^{44}$ represents a hydrogen atom, a $C_{2-6}$ alkoxycarbonyl group or a $C_{2-6}$ alkanoyl group, and $R^{1A}$ to $R^{3A}$, which may be the same or different, each represent a hydrogen atom, a $C_{2-8}$ alkanoyl group or a benzoyl group.

8. The method according to claim 3, wherein the compound of Formula (V) is a compound represented by the following formula:

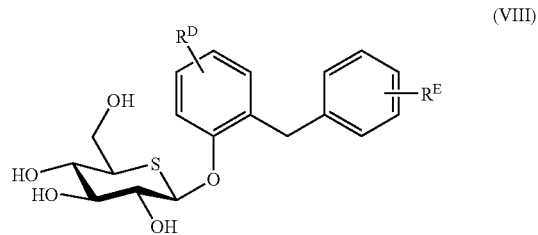

(VIII)

wherein $R^D$ represents a hydrogen atom, a halogen atom, a $C_{1-6}$ alkyl group or a hydroxy-$C_{1-4}$ alkyl group, and RE represents a hydrogen atom, a halogen atom, a $C_{1-6}$ alkyl group, a $C_{1-6}$ alkoxy group or a hydroxy-$C_{1-4}$ alkyl group.

9. The method according to claim 1, wherein Ar is an aryl group substituted with 1 to 4 electron-withdrawing groups.

10. The method according to claim 2, wherein $A^1$ is an aryl group substituted with 1 to 4 electron-withdrawing groups.

11. The method according to claim 5, wherein at least one of $R^{30}$, $R^{31}$, $R^{32}$ and $R^{33}$ is an electron-withdrawing group.

12. The method according to claim 6, wherein at least one of $R^{30A}$, $R^{31A}$, $R^{32A}$ and $R^{33A}$ is an electron-withdrawing group.

13. The method according to claim 7, wherein at least one of $R^{30B}$, $R^{31B}$, $R^{32B}$ and $R^{33B}$ is an electron-withdrawing group.

14. The method according to any one of claims 9 to 13, wherein the electron-withdrawing group is selected from a formyl group, a nitro group, a cyano group, a carboxyl group, a sulfonic acid group, —$^+NH_3$, —$^+N(CH_3)_3$, —$CF_3$, —$CCl_3$, —$COCH_3$, —$CO_2CH_3$, —$CO_2C_2H_3$, —$COPh$, —$SO_2CH_3$ and a halogen atom.

* * * * *

UNITED STATES PATENT AND TRADEMARK OFFICE
CERTIFICATE OF CORRECTION

PATENT NO. : 7,250,522 B2  Page 1 of 1
APPLICATION NO. : 10/521809
DATED : July 31, 2007
INVENTOR(S) : Masakazu Sato, Hiroyuki Kakinuma and Hajime Asanuma It is certified that error appears in the above-identified patent and that said Letters Patent is hereby corrected as shown below:

The General formula in the heading of the table at columns 33-34, 35-36, 37-38, 39-40, 41-42, 43-44, 45-46, 47-48, 49-50, and 51-52 correct as follows:

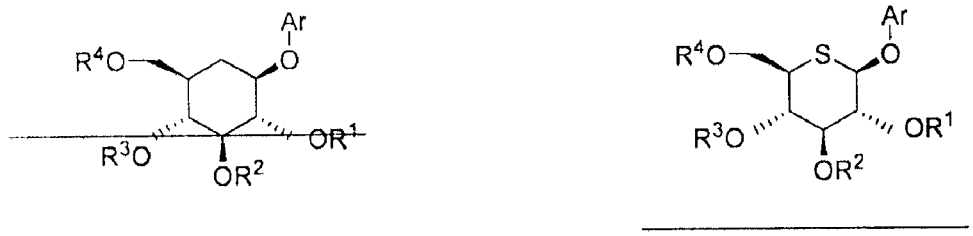

Signed and Sealed this

Second Day of September, 2008

JON W. DUDAS
*Director of the United States Patent and Trademark Office*